United States Patent
Nicholas et al.

(10) Patent No.: US 11,583,275 B2
(45) Date of Patent: Feb. 21, 2023

(54) SURGICAL INSTRUMENTS INCLUDING SENSOR ASSEMBLY

(71) Applicant: Covidien LP, Mansfield, MA (US)

(72) Inventors: David Nicholas, Trumbull, CT (US); Anthony Calderoni, Bristol, CT (US); Russell Pribanic, Roxbury, CT (US); David Zeichner, Oxford, CT (US); John Pantazis, Stratford, CT (US)

(73) Assignee: Covidien LP, Mansfield, MA (US)

( * ) Notice: Subject to any disclaimer, the term of this patent is extended or adjusted under 35 U.S.C. 154(b) by 199 days.

(21) Appl. No.: 17/102,813

(22) Filed: Nov. 24, 2020

(65) Prior Publication Data

US 2021/0196272 A1 Jul. 1, 2021

Related U.S. Application Data

(60) Provisional application No. 62/954,134, filed on Dec. 27, 2019.

(51) Int. Cl.
*A61B 17/072* (2006.01)
*A61B 17/00* (2006.01)

(52) U.S. Cl.
CPC ............... *A61B 17/07207* (2013.01); *A61B 2017/00039* (2013.01); *A61B 2017/00486* (2013.01);
(Continued)

(58) Field of Classification Search
CPC .... A61B 17/07207; A61B 2017/00039; A61B 2017/00486; A61B 2017/00876;
(Continued)

(56) References Cited

U.S. PATENT DOCUMENTS 2,957,353 A 10/1960 Babacz
3,111,328 A 11/1963 Di Rito et al.
(Continued)

FOREIGN PATENT DOCUMENTS

CA 2451558 A1 1/2003
CA 2839598 A1 * 7/2014 ....... A61B 17/07207
(Continued)

OTHER PUBLICATIONS

Extended European Search Report corresponding to International Application No. EP 14 18 4882.0 dated May 12, 2015.
(Continued)

*Primary Examiner* — Robert F Long
(74) *Attorney, Agent, or Firm* — Carter, DeLuca & Farrell LLP

(57) ABSTRACT

An adapter assembly includes a knob housing, an outer tube, an end effector, an articulation link, and a sensor assembly. The end effector is movable from a first position where the end effector is aligned with a longitudinal axis defined by the outer tube, to a second position where the end effector is disposed at an angle relative to the longitudinal axis. Longitudinal translation of the articulation link relative to the outer tube causes the end effector to move from its first position to its second position. The sensor assembly includes a first portion disposed in mechanical cooperation with the articulation link, and a second portion disposed at least partially within the outer tube. The sensor assembly is configured to determine an actual amount of articulation of the end effector based on a distance the articulation link move longitudinally relative to the outer tube.

20 Claims, 16 Drawing Sheets

(52) U.S. Cl.
CPC ............ *A61B 2017/00876* (2013.01); *A61B 2017/07257* (2013.01); *A61B 2017/07271* (2013.01); *A61B 2017/07285* (2013.01); *A61B 2562/0223* (2013.01)

(58) Field of Classification Search
CPC ........... A61B 2017/07257; A61B 2017/07271; A61B 2017/07285; A61B 2562/0223; A61B 2017/00017; A61B 2017/00398; A61B 2017/0046; A61B 2017/2927; A61B 2560/0223
USPC ............ 227/175.1–182.1; 606/139, 142, 143
See application file for complete search history.

(56) References Cited

U.S. PATENT DOCUMENTS

| | | |
|---|---|---|
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Mesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |

(56) References Cited

U.S. PATENT DOCUMENTS

| | | | |
|---|---|---|---|
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,403,949 B2 | 3/2013 | Palmer et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,480,703 B2 * | 7/2013 | Nicholas .......... A61B 17/07207 606/205 |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |

(56) References Cited

U.S. PATENT DOCUMENTS

| | | | |
|---|---|---|---|
| 9,282,963 B2 | 3/2016 | Bryant | |
| 9,295,522 B2 | 3/2016 | Kostrzewski | |
| 9,307,986 B2 | 4/2016 | Hall et al. | |
| 2001/0031975 A1 | 10/2001 | Whitman et al. | |
| 2002/0049454 A1 | 4/2002 | Whitman et al. | |
| 2002/0165541 A1 | 11/2002 | Whitman | |
| 2003/0038938 A1 | 2/2003 | Jung et al. | |
| 2003/0165794 A1 | 9/2003 | Matoba | |
| 2004/0034369 A1 | 2/2004 | Sauer et al. | |
| 2004/0111012 A1 | 6/2004 | Whitman | |
| 2004/0133189 A1 | 7/2004 | Sakurai | |
| 2004/0153124 A1 | 8/2004 | Whitman | |
| 2004/0176751 A1 | 9/2004 | Weitzner et al. | |
| 2004/0182588 A1* | 9/2004 | Tokunaga | B25B 23/1453 173/176 |
| 2004/0193146 A1 | 9/2004 | Lee et al. | |
| 2005/0125027 A1 | 6/2005 | Knodel et al. | |
| 2005/0131390 A1* | 6/2005 | Heinrich | A61B 17/07207 606/1 |
| 2005/0131442 A1 | 6/2005 | Yachia et al. | |
| 2006/0142656 A1 | 6/2006 | Malackowski et al. | |
| 2006/0142740 A1 | 6/2006 | Sherman et al. | |
| 2006/0142744 A1 | 6/2006 | Boutoussov | |
| 2006/0259073 A1 | 11/2006 | Miyamoto et al. | |
| 2006/0278680 A1 | 12/2006 | Viola et al. | |
| 2006/0284730 A1 | 12/2006 | Schmid et al. | |
| 2007/0023476 A1 | 2/2007 | Whitman et al. | |
| 2007/0023477 A1 | 2/2007 | Whitman et al. | |
| 2007/0027469 A1 | 2/2007 | Smith et al. | |
| 2007/0029363 A1 | 2/2007 | Popov | |
| 2007/0084897 A1 | 4/2007 | Shelton et al. | |
| 2007/0102472 A1 | 5/2007 | Shelton | |
| 2007/0152014 A1 | 7/2007 | Gillum et al. | |
| 2007/0175947 A1 | 8/2007 | Ortiz et al. | |
| 2007/0175949 A1 | 8/2007 | Shelton et al. | |
| 2007/0175950 A1 | 8/2007 | Shelton et al. | |
| 2007/0175951 A1 | 8/2007 | Shelton et al. | |
| 2007/0175955 A1 | 8/2007 | Shelton et al. | |
| 2007/0270784 A1 | 11/2007 | Smith et al. | |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0058801 A1 | 3/2008 | Taylor et al. | |
| 2008/0109012 A1 | 5/2008 | Falco et al. | |
| 2008/0110958 A1 | 5/2008 | McKenna et al. | |
| 2008/0147089 A1 | 6/2008 | Loh et al. | |
| 2008/0167736 A1 | 7/2008 | Swayze et al. | |
| 2008/0185419 A1 | 8/2008 | Smith et al. | |
| 2008/0188841 A1 | 8/2008 | Tomasello et al. | |
| 2008/0197167 A1 | 8/2008 | Viola et al. | |
| 2008/0208195 A1 | 8/2008 | Shores et al. | |
| 2008/0237296 A1 | 10/2008 | Boudreaux et al. | |
| 2008/0251561 A1 | 10/2008 | Eades et al. | |
| 2008/0255413 A1 | 10/2008 | Zemlok et al. | |
| 2008/0255607 A1 | 10/2008 | Zemlok | |
| 2008/0262654 A1 | 10/2008 | Omori et al. | |
| 2008/0308603 A1 | 12/2008 | Shelton et al. | |
| 2009/0012533 A1 | 1/2009 | Barbagli | |
| 2009/0090763 A1* | 4/2009 | Zemlok | A61B 17/07207 227/175.2 |
| 2009/0099876 A1 | 4/2009 | Whitman | |
| 2009/0138006 A1 | 5/2009 | Bales et al. | |
| 2009/0171147 A1 | 7/2009 | Lee et al. | |
| 2009/0182193 A1 | 7/2009 | Whitman et al. | |
| 2009/0209946 A1 | 8/2009 | Swayze et al. | |
| 2009/0209990 A1 | 8/2009 | Yates et al. | |
| 2009/0254094 A1 | 10/2009 | Knapp et al. | |
| 2009/0299141 A1 | 12/2009 | Downey et al. | |
| 2010/0023022 A1 | 1/2010 | Zeiner et al. | |
| 2010/0069942 A1 | 3/2010 | Shelton, IV | |
| 2010/0193568 A1 | 8/2010 | Scheib et al. | |
| 2010/0211053 A1 | 8/2010 | Ross et al. | |
| 2010/0225073 A1 | 9/2010 | Porter et al. | |
| 2011/0006101 A1 | 1/2011 | Hall et al. | |
| 2011/0017801 A1 | 1/2011 | Zemlok et al. | |
| 2011/0062211 A1 | 3/2011 | Ross et al. | |
| 2011/0071508 A1 | 3/2011 | Duval et al. | |
| 2011/0077673 A1 | 3/2011 | Grubac et al. | |
| 2011/0121049 A1 | 5/2011 | Malinouskas et al. | |
| 2011/0125138 A1 | 5/2011 | Malinouskas et al. | |
| 2011/0139851 A1 | 6/2011 | McCuen | |
| 2011/0155783 A1 | 6/2011 | Rajappa et al. | |
| 2011/0155786 A1 | 6/2011 | Shelton, IV | |
| 2011/0172648 A1 | 7/2011 | Jeong | |
| 2011/0174009 A1 | 7/2011 | Iizuka et al. | |
| 2011/0174099 A1 | 7/2011 | Ross et al. | |
| 2011/0184245 A1 | 7/2011 | Xia et al. | |
| 2011/0204119 A1 | 8/2011 | McCuen | |
| 2011/0218522 A1 | 9/2011 | Whitman | |
| 2011/0276057 A1 | 11/2011 | Conlon et al. | |
| 2011/0290854 A1 | 12/2011 | Timm et al. | |
| 2011/0295242 A1 | 12/2011 | Spivey et al. | |
| 2011/0295269 A1 | 12/2011 | Swensgard et al. | |
| 2012/0000962 A1 | 1/2012 | Racenet et al. | |
| 2012/0074199 A1 | 3/2012 | Olson et al. | |
| 2012/0089131 A1 | 4/2012 | Zemlok et al. | |
| 2012/0104071 A1 | 5/2012 | Bryant | |
| 2012/0116368 A1 | 5/2012 | Viola | |
| 2012/0143002 A1 | 6/2012 | Aranyi et al. | |
| 2012/0172924 A1 | 7/2012 | Allen, IV | |
| 2012/0211542 A1 | 8/2012 | Racenet | |
| 2012/0223121 A1 | 9/2012 | Viola et al. | |
| 2012/0245428 A1 | 9/2012 | Smith et al. | |
| 2012/0253329 A1 | 10/2012 | Zemlok et al. | |
| 2012/0310220 A1 | 12/2012 | Malkowski et al. | |
| 2012/0323226 A1 | 12/2012 | Chowaniec et al. | |
| 2012/0330285 A1 | 12/2012 | Hartoumbekis et al. | |
| 2013/0093149 A1 | 4/2013 | Saur et al. | |
| 2013/0181035 A1 | 7/2013 | Milliman | |
| 2013/0184704 A1 | 7/2013 | Beardsley et al. | |
| 2013/0214025 A1 | 8/2013 | Zemlok et al. | |
| 2013/0274722 A1 | 10/2013 | Kostrzewski et al. | |
| 2013/0282052 A1 | 10/2013 | Aranyi et al. | |
| 2013/0292451 A1 | 11/2013 | Viola et al. | |
| 2013/0313304 A1 | 11/2013 | Shelton, IV et al. | |
| 2013/0317486 A1 | 11/2013 | Nicholas et al. | |
| 2013/0319706 A1 | 12/2013 | Nicholas et al. | |
| 2013/0324978 A1 | 12/2013 | Nicholas et al. | |
| 2013/0324979 A1 | 12/2013 | Nicholas et al. | |
| 2013/0334281 A1 | 12/2013 | Williams | |
| 2014/0012236 A1 | 1/2014 | Williams et al. | |
| 2014/0012237 A1 | 1/2014 | Pribanic et al. | |
| 2014/0012289 A1 | 1/2014 | Snow et al. | |
| 2014/0025046 A1 | 1/2014 | Williams et al. | |
| 2014/0110455 A1 | 4/2014 | Ingmanson et al. | |
| 2014/0207125 A1 | 7/2014 | Applegate et al. | |
| 2014/0207182 A1 | 7/2014 | Zergiebel et al. | |
| 2014/0207185 A1 | 7/2014 | Goble et al. | |
| 2014/0236174 A1 | 8/2014 | Williams et al. | |
| 2014/0276932 A1 | 9/2014 | Williams et al. | |
| 2014/0299647 A1 | 10/2014 | Scirica et al. | |
| 2014/0303668 A1 | 10/2014 | Nicholas et al. | |
| 2014/0350530 A1* | 11/2014 | Ross | A61B 17/07207 606/1 |
| 2014/0358129 A1 | 12/2014 | Zergiebel et al. | |
| 2014/0361068 A1 | 12/2014 | Aranyi et al. | |
| 2014/0365235 A1 | 12/2014 | DeBoer et al. | |
| 2014/0373652 A1 | 12/2014 | Zergiebel et al. | |
| 2015/0014392 A1 | 1/2015 | Williams et al. | |
| 2015/0048144 A1 | 2/2015 | Whitman | |
| 2015/0076205 A1 | 3/2015 | Zergiebel | |
| 2015/0080912 A1 | 3/2015 | Sapre | |
| 2015/0105630 A1* | 4/2015 | Kummerl | A61B 5/02438 600/502 |
| 2015/0112381 A1 | 4/2015 | Richard | |
| 2015/0122870 A1 | 5/2015 | Zemlok et al. | |
| 2015/0133224 A1 | 5/2015 | Whitman et al. | |
| 2015/0150547 A1 | 6/2015 | Ingmanson et al. | |
| 2015/0150574 A1 | 6/2015 | Richard et al. | |
| 2015/0157320 A1 | 6/2015 | Zergiebel et al. | |
| 2015/0157321 A1 | 6/2015 | Zergiebel et al. | |
| 2015/0164502 A1 | 6/2015 | Richard et al. | |
| 2015/0201931 A1 | 7/2015 | Zergiebel et al. | |

(56) References Cited

U.S. PATENT DOCUMENTS

| | | | |
|---|---|---|---|
| 2015/0272577 | A1 | 10/2015 | Zemlok et al. |
| 2015/0297199 | A1 | 10/2015 | Nicholas et al. |
| 2015/0303996 | A1 | 10/2015 | Calderoni |
| 2015/0320420 | A1 | 11/2015 | Penna et al. |
| 2015/0327850 | A1 | 11/2015 | Kostrzewski |
| 2015/0342601 | A1 | 12/2015 | Williams et al. |
| 2015/0342603 | A1 | 12/2015 | Zergiebel et al. |
| 2015/0374366 | A1 | 12/2015 | Zergiebel et al. |
| 2015/0374370 | A1 | 12/2015 | Zergiebel et al. |
| 2015/0374371 | A1 | 12/2015 | Richard et al. |
| 2015/0374372 | A1 | 12/2015 | Zergiebel et al. |
| 2015/0374449 | A1 | 12/2015 | Chowaniec et al. |
| 2015/0380187 | A1 | 12/2015 | Zergiebel et al. |
| 2016/0095585 | A1 | 4/2016 | Zergiebel et al. |
| 2016/0095596 | A1 | 4/2016 | Scirica et al. |
| 2016/0106406 | A1 | 4/2016 | Cabrera et al. |
| 2016/0113648 | A1 | 4/2016 | Zergiebel et al. |
| 2016/0113649 | A1 | 4/2016 | Zergiebel et al. |
| 2016/0310134 | A1 | 10/2016 | Contini et al. |
| 2017/0020614 | A1* | 1/2017 | Jackson ............. A61B 34/30 |
| 2018/0360451 | A1 | 12/2018 | Shelton, IV et al. |
| 2019/0076135 | A1* | 3/2019 | Ross ............. A61B 17/00 |
| 2019/0183503 | A1 | 6/2019 | Shelton, IV et al. |
| 2020/0405293 | A1 | 12/2020 | Shelton, IV et al. |

FOREIGN PATENT DOCUMENTS

| | | | | |
|---|---|---|---|---|
| CN | 1547454 | A | 11/2004 | |
| CN | 1957854 | A | 5/2007 | |
| CN | 101495046 | A | 7/2009 | |
| CN | 101856251 | A | 10/2010 | |
| CN | 102247182 | A | 11/2011 | |
| DE | 102008053842 | A1 | 5/2010 | |
| EP | 0705571 | A1 | 4/1996 | |
| EP | 1563793 | A1 | 8/2005 | |
| EP | 1759652 | A2 | 3/2007 | |
| EP | 1769754 | A1 | 4/2007 | |
| EP | 1908412 | A2 | 4/2008 | |
| EP | 1917929 | A1 | 5/2008 | |
| EP | 1952769 | A2 | 8/2008 | |
| EP | 2090247 | A1 | 8/2009 | |
| EP | 2245994 | A1 | 11/2010 | |
| EP | 2316345 | A1 | 5/2011 | |
| EP | 2377472 | A1 | 10/2011 | |
| EP | 2668910 | A2 | 12/2013 | |
| EP | 2815705 | A1 | 12/2014 | |
| ES | 2333509 | A1 | 2/2010 | |
| FR | 2861574 | A1 | 5/2005 | |
| JP | 2005125075 | A | 5/2005 | |
| KR | 20120022521 | A | 3/2012 | |
| WO | 2011108840 | A2 | 9/2011 | |
| WO | 2012/040984 | A1 | 4/2012 | |
| WO | WO-2022070082 | A1 * | 4/2022 | ......... A61B 17/1155 |

OTHER PUBLICATIONS

Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 //93.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
European Search Report corresponding to EP 15 184 915.5-1654 dated Sep. 16, 2016.
Australian Examination Report No. 1 corresponding to International Application No. AU 2013205872 dated Oct. 19, 2016.
Australian Examination Report from Appl. No. AU 2013205840 dated Nov. 3, 2016.
Notification of Transmittal of the International Search Report and The Written Opinion of the International Searching Authority issued in corresponding application No. PCT/US2016/027042 dated Jul. 12, 2016.

(56) References Cited

OTHER PUBLICATIONS

Extended European Search Report dated Apr. 29, 2021 corresponding to counterpart Patent Application EP 20215390.4.

* cited by examiner

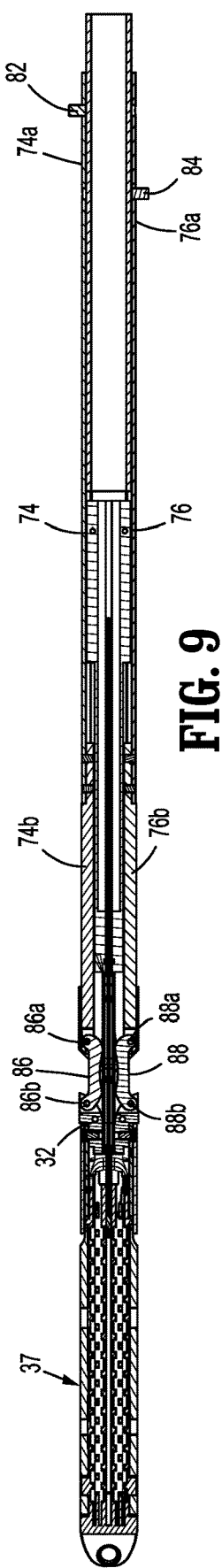
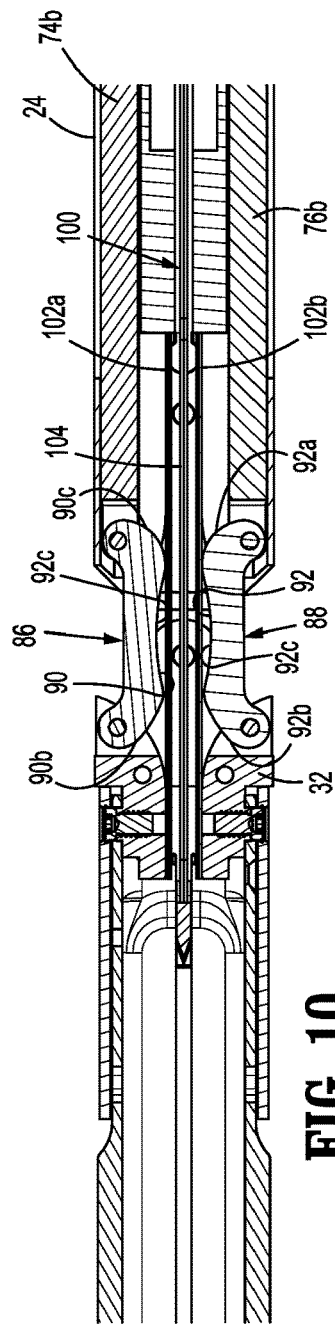
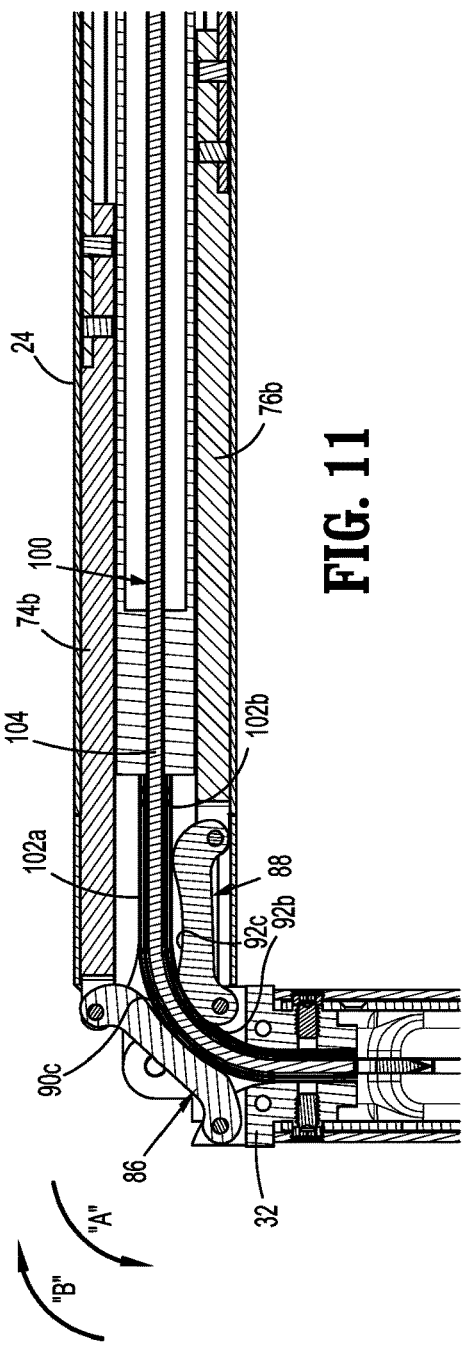
FIG. 9
FIG. 10
FIG. 11

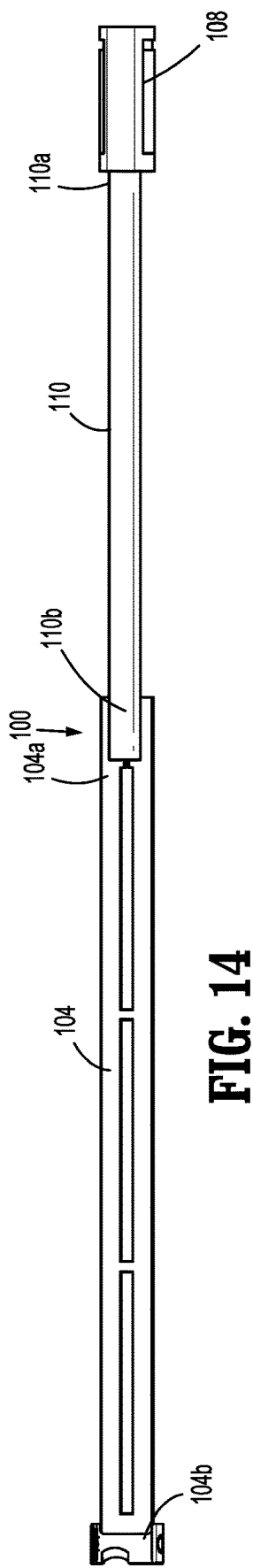
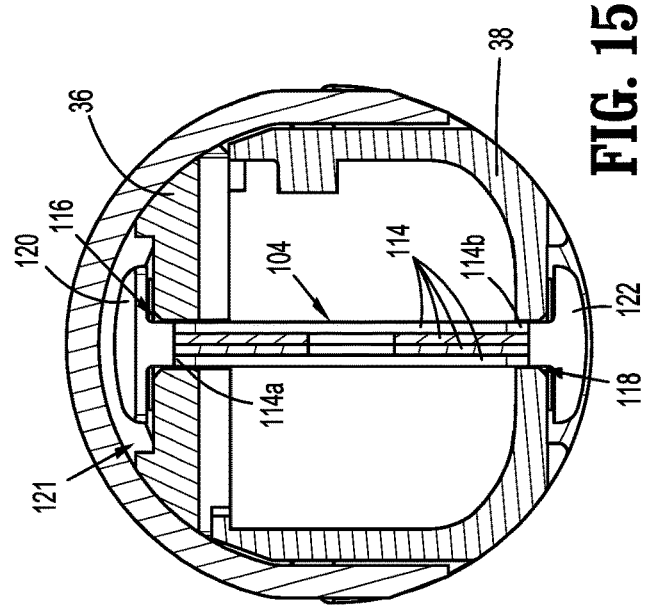
FIG. 14
FIG. 15

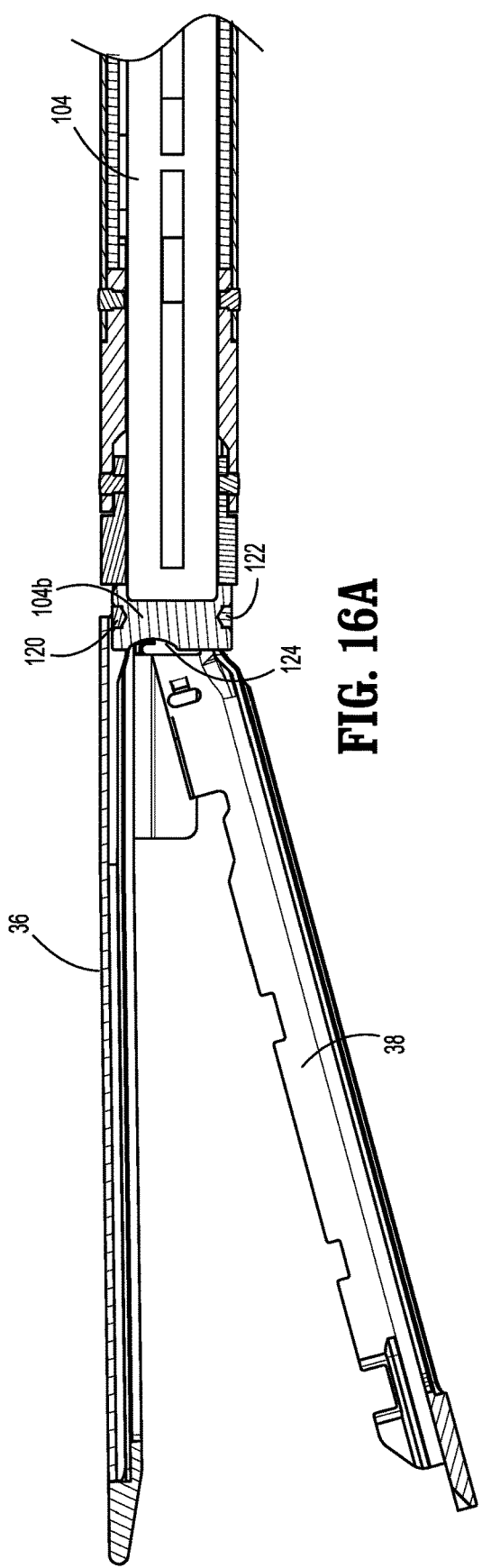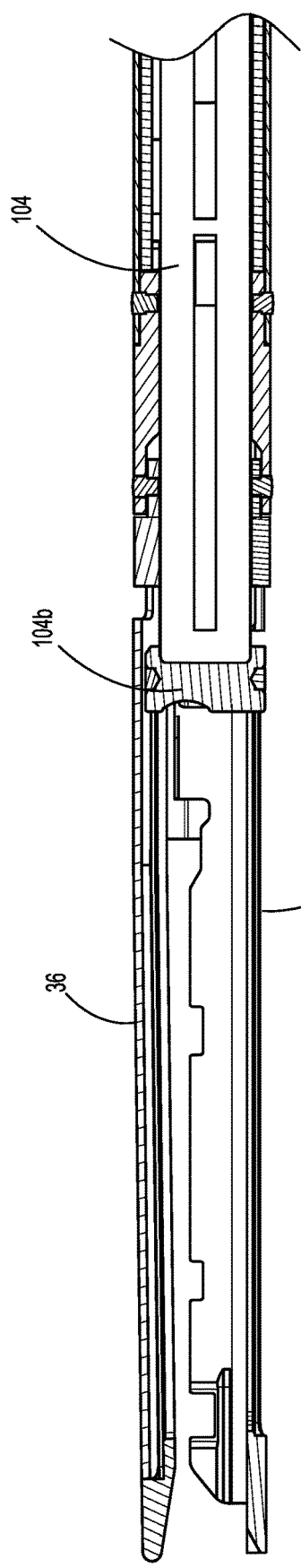

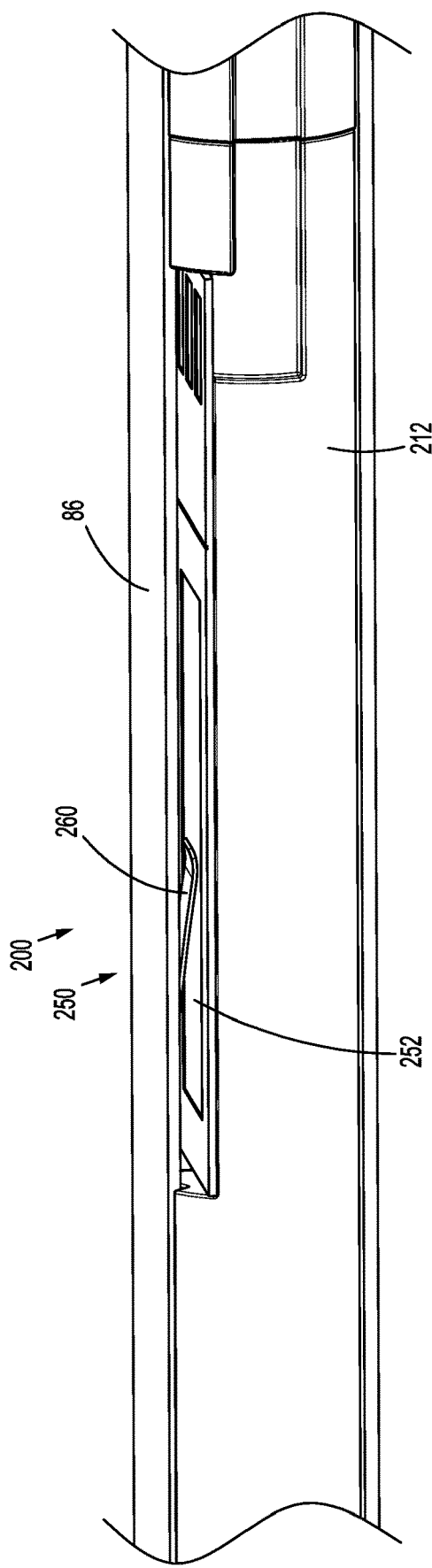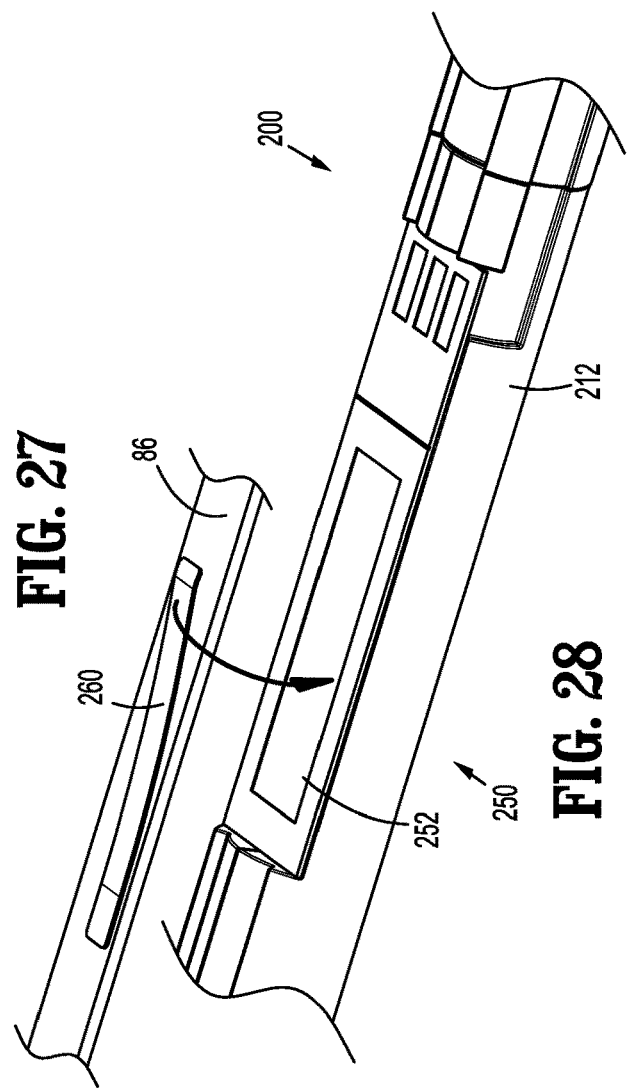
FIG. 27
FIG. 28

SURGICAL INSTRUMENTS INCLUDING SENSOR ASSEMBLY

CROSS-REFERENCE TO RELATED APPLICATIONS

This application claims the benefit of and priority to U.S. Provisional Patent Application Ser. No. 62/954,134 filed Dec. 27, 2019, the entire disclosure of which is incorporated by reference herein.

BACKGROUND

Technical Field

The present disclosure relates generally to surgical instruments for endoscopic use and, more specifically, to surgical instruments including adapter assemblies that articulate an attached surgical loading unit.

Background of Related Art

Various types of surgical instruments used to endoscopically treat tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument. Typically, surgical stapling instruments include an end effector having an anvil assembly and a cartridge assembly for supporting an array of surgical staples, an approximation mechanism for approximating the cartridge and anvil assemblies, a rotation assembly for rotating the cartridge and anvil assemblies about an axis, and a firing mechanism for ejecting the surgical staples from the cartridge assembly.

During laparoscopic or endoscopic surgical procedures, access to a surgical site is achieved through a small incision or through a narrow cannula inserted through a small entrance wound in a patient. Because of limited area available to access the surgical site, many endoscopic instruments include mechanisms for articulating the end effector of the instrument in relation to a body portion of the instrument to improve access to tissue to be treated. Some instruments include a motor or drive element for causing articulation of the end effector, and also include a rotation assembly for causing rotation of the end effector.

It would be beneficial to provide an improved surgical instrument or adapter assembly which can detect and/or correct any undesired partial articulation of the end effector.

SUMMARY

The present disclosure relates to an adapter assembly configured to mechanically engage a surgical instrument. The adapter assembly includes a knob housing, an outer tube, an end effector, an articulation link, and a sensor assembly. The outer tube extends distally from the knob housing and defines a longitudinal axis. The end effector extends distally from the outer tube, and is movable from a first position where the end effector is aligned with the longitudinal axis, to a second position where the end effector is disposed at an angle relative to the longitudinal axis. The articulation link extends through at least a portion of the outer tube and is disposed in mechanical cooperation with the end effector. Longitudinal translation of the articulation link relative to the outer tube causes the end effector to move from its first position to its second position. The sensor assembly includes a first portion disposed in mechanical cooperation with the articulation link, and a second portion disposed at least partially within the outer tube. The sensor assembly is configured to determine an actual amount of articulation of the end effector based on a distance the articulation link moves longitudinally relative to the outer tube.

In disclosed embodiments, the sensor assembly is configured to communicate with software that compares the actual amount of articulation of the end effector with a desired amount of articulation of the end effector. It is disclosed that the software is disposed on a printed circuit board disposed at least partially within the knob housing.

It is also disclosed that one of the first portion or the second portion of the sensor assembly is a magnet, and the other of the first portion or the second portion of the sensor assembly is a magnetoresistive sensor.

It is further disclosed that one of the first portion or the second portion of the sensor assembly is a leaf spring, and the other of the first portion or the second portion of the sensor assembly is a thin-pot resistive sensor.

Additionally, it is disclosed that the adapter assembly includes a second sensor assembly disposed at least partially within the knob housing. The second sensor assembly is configured to detect manual rotation of the knob housing relative to the outer tube. In embodiments, the second sensor assembly includes at least one sensor and at least one magnet, and the at least one sensor of the second sensor assembly includes at least two Hall effect sensors. It is also disclosed that the at least one magnet of the second sensor assembly includes a refrigerator-type magnet. In further embodiments, the software is disposed on a printed circuit board disposed at least partially within the knob housing, and the at least two Hall effect sensors are disposed on the printed circuit board.

The present disclosure also relates to a surgical instrument including a handle assembly and an adapter assembly. The handle assembly includes a first drive member. The adapter assembly is configured to selectively engage the handle assembly and includes a knob housing, an outer tube, an end effector, an articulation link, a ring gear, and a sensor assembly. The outer tube extends distally from the knob housing and defines a longitudinal axis. The end effector extends distally from the outer tube, and is movable from a first position where the end effector is aligned with the longitudinal axis, to a second position where the end effector is disposed at an angle relative to the longitudinal axis. The articulation link extends through at least a portion of the outer tube and is disposed in mechanical cooperation with the end effector. Longitudinal translation of the articulation link relative to the outer tube causes the end effector to move from its first position to its second position. The ring gear is disposed at least partially within the knob housing and is in mechanical cooperation with the first drive member when the adapter assembly is engaged with the handle assembly. Rotation of the first drive member causes rotation of the ring gear about the longitudinal axis, which causes longitudinal translation of the articulation link. The sensor assembly includes a first portion disposed in mechanical cooperation with the articulation link, and a second portion disposed at least partially within the outer tube. The sensor assembly is configured to determine an actual amount of articulation of the end effector based on a distance the articulation link moves longitudinally relative to the outer tube.

In disclosed embodiments, manual rotation of the knob housing causes undesired articulation of the end effector. In embodiments, the sensor assembly is configured to communicate with software, and the software compares the actual amount of articulation of the end effector with a desired amount of articulation of the end effector. It is further disclosed that the software is configured to instruct the first drive member of the surgical instrument to move the articulation link such that the actual articulation of the end effector equals the desired articulation of the end effector.

It is also disclosed that the surgical instrument includes a second sensor assembly disposed at least partially within the knob housing. The second sensor assembly is configured to detect manual rotation of the knob housing relative to the outer tube. In embodiments, the second sensor assembly includes at least one sensor and at least one magnet. It is further disclosed that the at least one sensor of the second sensor assembly includes at least two Hall effect sensors, and that the at least one magnet of the second sensor assembly includes a refrigerator-type magnet (e.g., a magnet having appropriately alternating north/south oriented poles).

In disclosed embodiments, one of the first portion or the second portion of the sensor assembly is a magnet, and the other of the first portion or the second portion of the sensor assembly is a magnetoresistive sensor.

In additional embodiments, one of the first portion or the second portion of the sensor assembly is a leaf spring, and the other of the first portion or the second portion of the sensor assembly is a thin-pot resistive senor.

BRIEF DESCRIPTION OF THE DRAWINGS

Surgical instruments including embodiments of the presently disclosed adapter assemblies are disclosed herein with reference to the drawings, wherein:

FIG. 9 is a top, cross-sectional view of a distal section of the adapter assembly and the surgical loading unit of FIG. 1;

FIG. 10 is an enlarged, top, cross-sectional view of the adapter assembly and surgical loading unit of FIG. 9;

FIG. 11 is a top, cross-sectional view of the distal section of the adapter assembly and the surgical loading unit of FIG. 9, with the surgical loading unit illustrated in an articulated position relative to the adapter assembly;

FIG. 14 is a side view of an I-beam assembly of the adapter assembly of FIG. 12;

FIG. 15 is a front, cross-sectional view of the surgical loading unit and the I-beam assembly of FIG. 14;

FIG. 16A is a side, cross-sectional view of the surgical loading unit in an open configuration, illustrating the I-beam assembly in a retracted position;

FIG. 16B is a side, cross-sectional view of the surgical loading unit in a closed configuration, illustrating the I-beam assembly in an advanced position;

FIG. 27 is a perspective view of another embodiment of a sensor assembly for use with the adapter assembly of FIG. 20; and FIG. 28 is a perspective, assembly view of the sensor assembly of FIG. 27.

DETAILED DESCRIPTION

Persons skilled in the art will understand that the adapter assemblies and surgical loading units specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the described embodiments. Accordingly, the disclosure is not to be limited by what has been particularly shown and described, except as indicated by the appended claims.

As used herein, the term "distal" refers to that portion of the surgical instrument which is farthest from a clinician, while the term "proximal" refers to that portion of the surgical instrument which is closest to the clinician. In addition, as used herein, the term clinician refers to medical staff including doctors, nurses and support personnel.

The present disclosure is directed to a surgical instrument including an adapter assembly configured to be actuated by a hand-held actuator or a surgical robotic system, and a surgical loading unit coupled to the adapter assembly. The adapter assembly includes an articulation mechanism that drives an articulation of the surgical loading unit relative to the adapter assembly. The articulation mechanism includes a cam housing that defines a pair of cam slots, each of which receiving a corresponding pin of a pair of elongate shafts. As the cam housing rotates, the cam slots drive an opposing longitudinal motion of the pair of elongate shafts, which articulate the surgical loading unit. Additional advantages of the presently disclosed surgical instruments and components thereof are described below.

Figure 1:
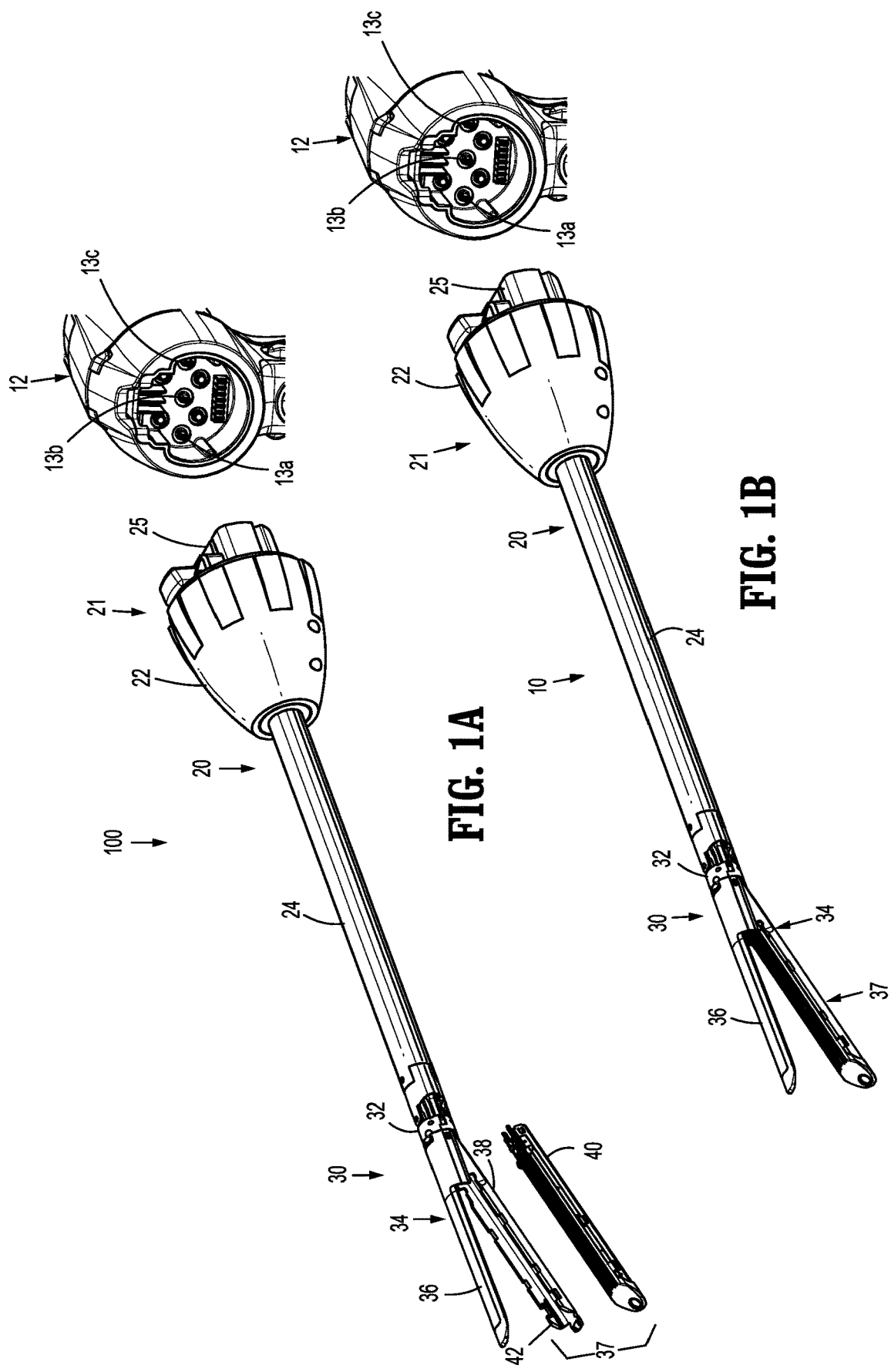
FIG. 1A is a perspective view of a surgical instrument including an adapter assembly and a surgical loading unit, with a staple cartridge body of the surgical loading unit shown removed from a chassis of the surgical loading unit.
FIG. 1B is a perspective view of the surgical instrument of FIG. 1A, with the staple cartridge body of the surgical loading unit shown installed in the chassis.

FIGS. 1A and 1B illustrate a surgical instrument 10 including a handle assembly 12, an adapter assembly 20 configured to be coupled to the handle assembly 12, and a surgical loading unit 30 pivotably coupled to the adapter assembly 20. While the depicted surgical instrument 10 may be configured to fire staples, it is contemplated that the surgical instrument 10 may be adapted to fire any other suitable fastener such as clips and two-part fasteners. Additionally, while the figures depict a linear surgical stapling instrument 10, it is envisioned that certain components described herein may be adapted for use in other types of endoscopic surgical instruments including non-linear surgical stapler loading units, endoscopic forceps, graspers, dissectors, other types of surgical stapling instruments, powered vessel sealing and/or cutting devices, etc.

Generally, the adapter assembly 20 of the surgical instrument 10 includes an outer housing 21 and an outer tube 24 extending distally from the outer housing 21. The outer housing 21 includes a knob housing 22 and a coupling mechanism 25 extending proximally from the knob housing 22 and configured to be operably coupled to the handle assembly 12 or a surgical robotic system (not shown) responsible for actuating the surgical instrument 10. The outer tube 24 has a proximal end portion fixed within the distal end portion of the knob housing 22. In other embodiments, the outer tube 24 may be rotatable relative to and within the knob housing 22. The surgical loading unit 30 is adapted to be attached to a distal end portion of the outer tube 24 of the adapter assembly 20 and may be configured for a single use, or may be configured to be used more than once.

The surgical loading unit 30 includes a collar 32 pivotably coupled to the distal end portion of the outer tube 24 and an end effector 34 supported on the collar 32. The end effector 34 includes an anvil plate 36 non-rotationally coupled to the collar 32, and a staple cartridge assembly 37 disposed in opposed relation with the anvil plate 36. The staple cartridge assembly 37 has a chassis 38 pivotably coupled to the collar 32 and a staple cartridge body 40 configured for removable receipt in a channel 42 of the chassis 38.

For a detailed description of the handle assembly 12, reference may be made to U.S. Patent Application Publication No. 2015/0157320, filed on Nov. 21, 2014, and U.S. Patent Application Publication No. 2016/0310134, filed on Apr. 12, 2016, the entire contents of each of which being incorporated by reference herein.

Figure 2:
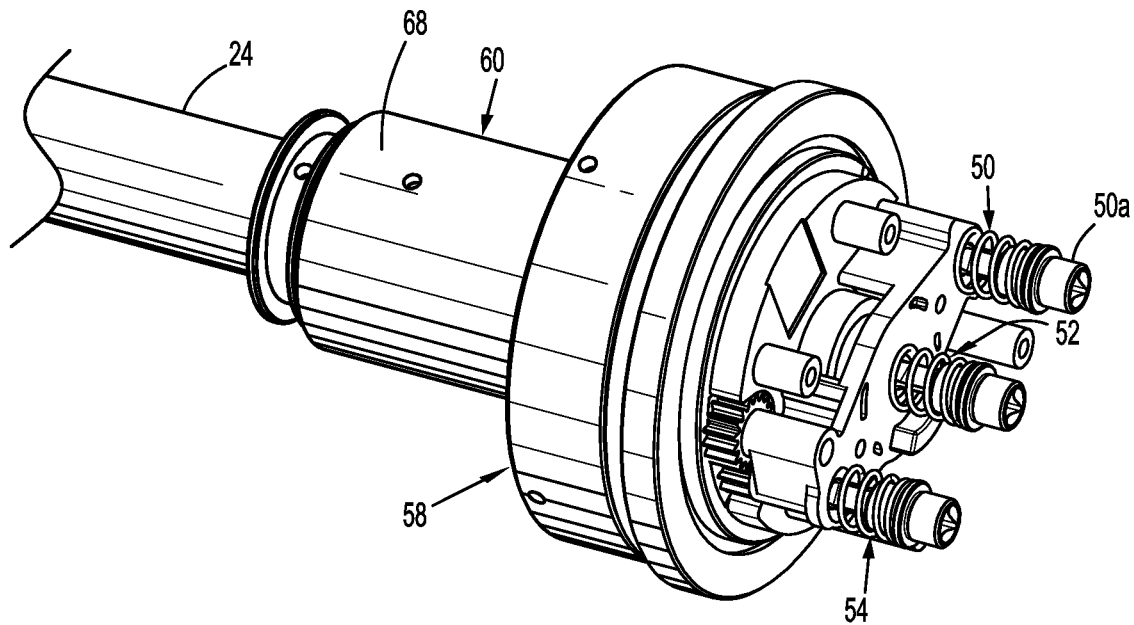
FIG. 2 is a perspective view of internal components of the adapter assembly of FIG. 1A.
Figure 3:
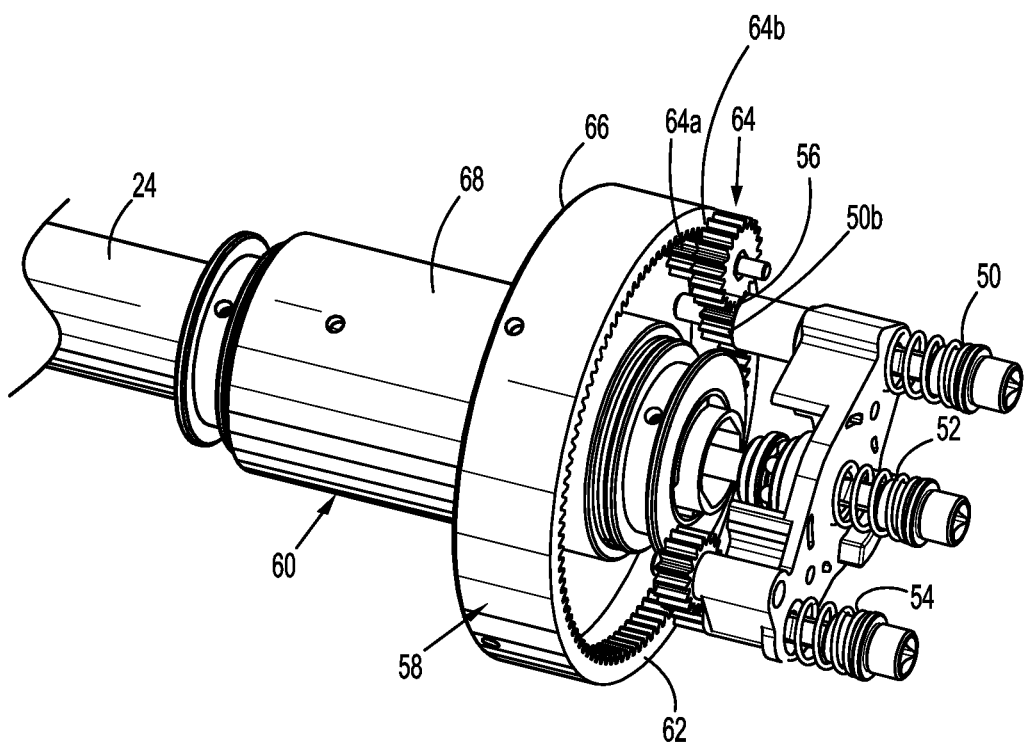
FIG. 3 is a perspective view, with parts removed, of the internal components of the adapter assembly shown in FIG. 2.
Figure 4:
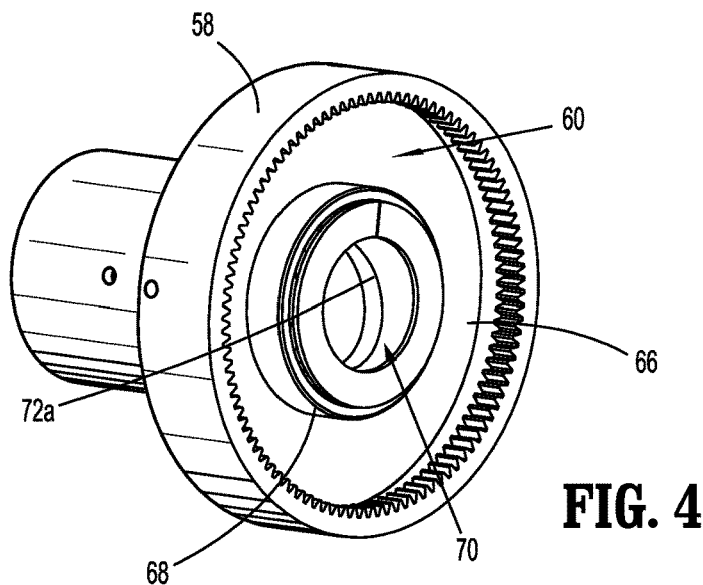
FIG. 4 is a rear, perspective view of a cam housing and a ring gear of the internal components of the adapter assembly of FIG. 2.
Figure 5:
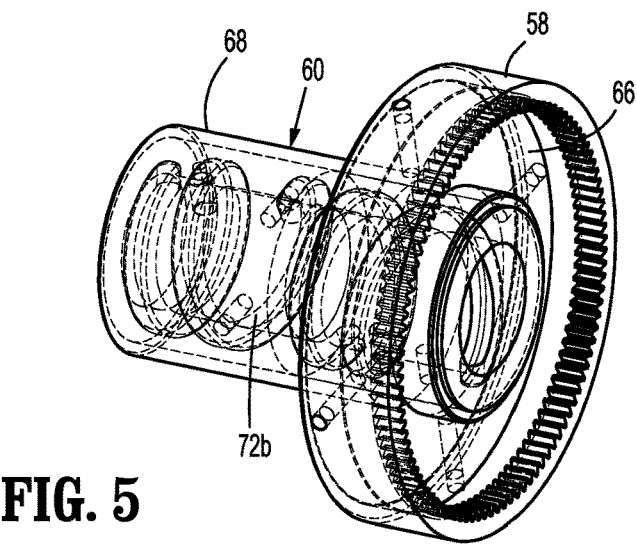
FIG. 5 is a side, perspective view of the cam housing and ring gear of FIG. 4 shown in phantom.
Figure 6:
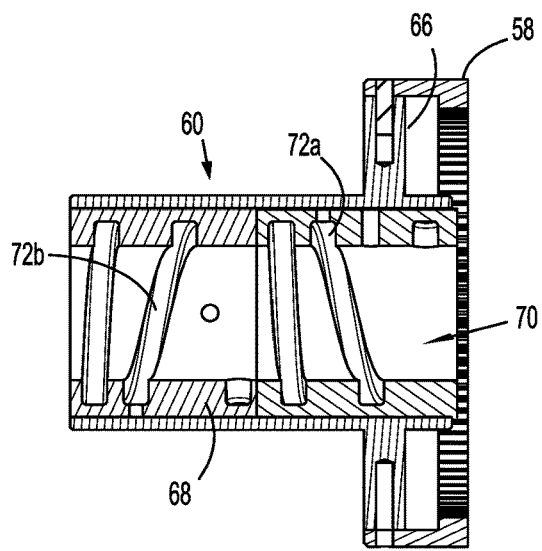
FIG. 6 is a side, cross-sectional view of the cam housing and ring gear of FIG. 4.
Figure 7:
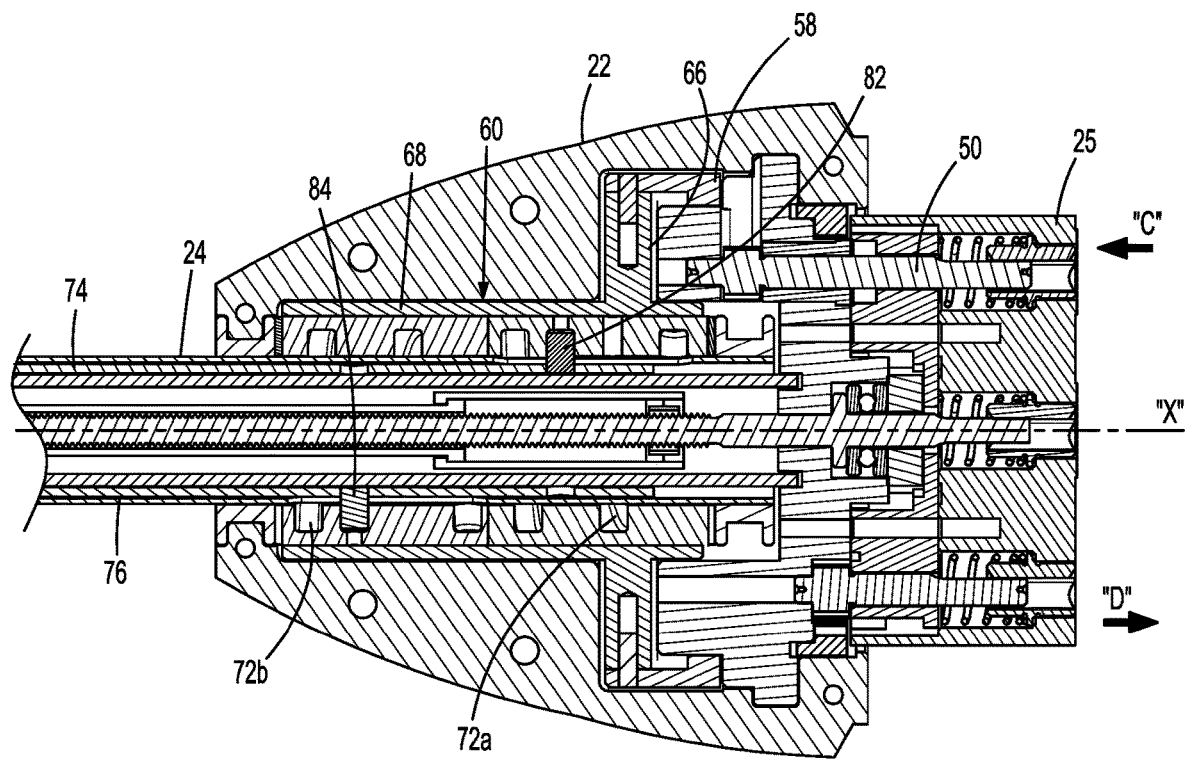
FIG. 7 is a side, cross-sectional view of a proximal section of the adapter assembly of FIG. 1A.
Figure 8:
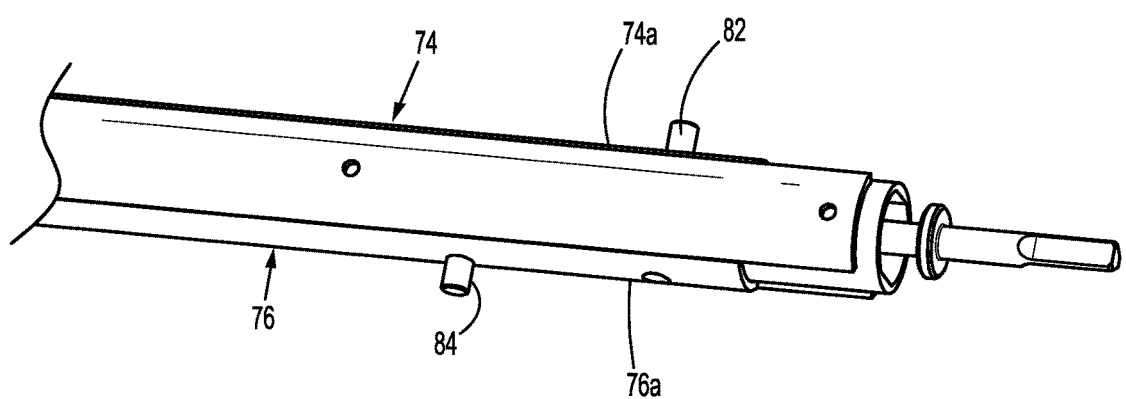
FIG. 8 is a side, perspective view of a pair of first and second elongate shafts of the adapter assembly of FIG. 7.
Figure 12:
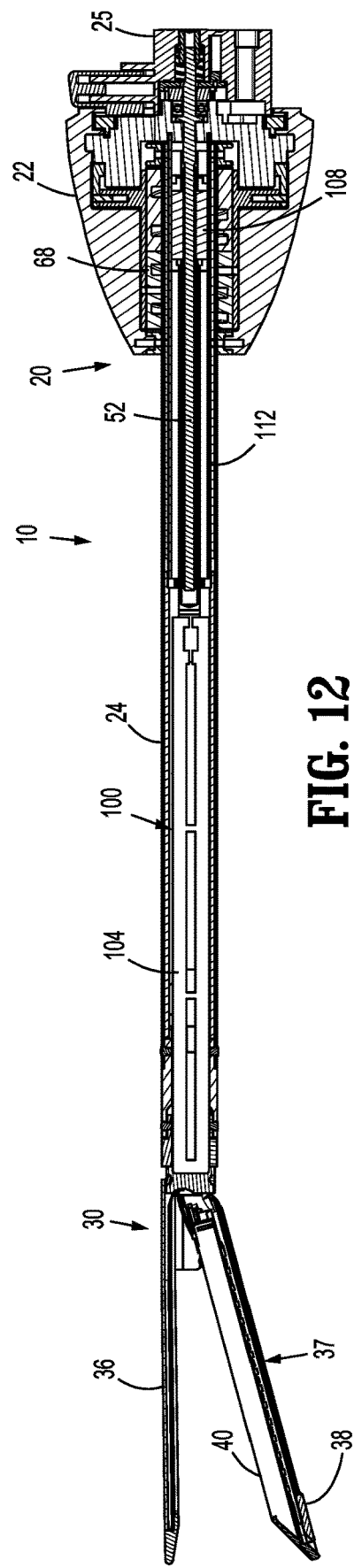
FIG. 12 is a side, cross-sectional view of the adapter assembly of FIG. 1A.
Figure 13:
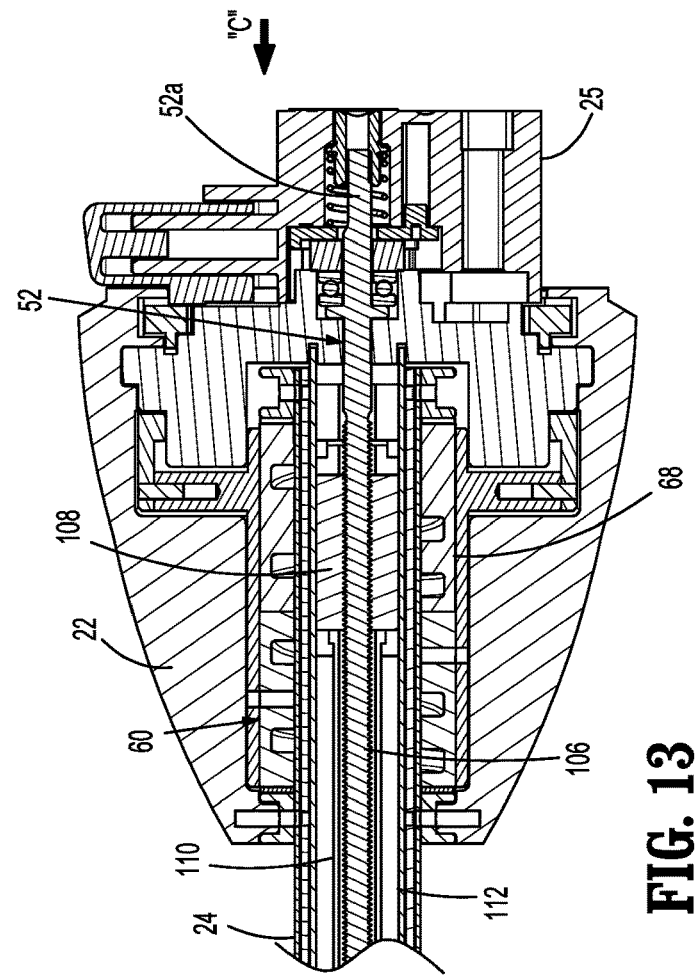
FIG. 13 is a side, cross-sectional view of the proximal section of the adapter assembly of FIG. 12.

With reference to FIGS. 2 and 3, the articulation mechanism of the adapter assembly 20 will now be described. The adapter assembly 20 includes an articulation input shaft 50, a firing input shaft 52, and a rotation input shaft 54 each rotationally supported in the coupling mechanism 25 of the outer housing 21 (FIG. 1A). The articulation input shaft 50 has a proximal end portion 50a configured to be drivingly coupled to a corresponding drive member 13a of the handle assembly 12 to effect a rotation of the articulation input shaft 50. The articulation input shaft 50 has a distal end portion 50b having a gear 56 (e.g., a spur gear) fixed thereabout.

The adapter assembly 20 includes a ring gear 58 operably coupled to the articulation input shaft 50 and non-rotationally coupled to a cam housing 60. The ring gear 58 has an inner surface defining gear teeth 62 interfacing with gear teeth of a first gear 64a of a spur gear cluster 64. The spur gear cluster 64 has a second gear 64b fixed to and disposed adjacent the first gear 64a and having a larger diameter than the first gear 64a. The second gear 64b of the spur gear cluster 64 interfaces with the gear 56 non-rotationally fixed about the distal end portion 50b of the articulation input shaft 50. As such, a rotation of the articulation input shaft 50 rotates the first gear 64a and second gear 64b of the spur gear cluster 64, which, in turn, drives a rotation of the ring gear 58.

With reference to FIGS. 2-7, the cam housing 60 of the adapter assembly 20 is rotationally supported in the knob housing 22. The cam housing 60 includes an annular plate or disc 66 and a tubular shaft 68 extending distally from the annular plate 66. The annular plate 66 may be disposed within, and pinned to, the ring gear 58, such that the cam housing 60 rotates with a rotation of the ring gear 58. The tubular shaft 68 of the cam housing 60 defines a longitudinally-extending channel 70 therethrough. The channel 70 is dimensioned for receipt of various components of the articulation and firing mechanisms of the adapter assembly 20, thereby allowing for a more compact design of the adapter assembly 20.

With reference to FIGS. 4-7, the tubular shaft 68 of the cam housing 60 defines a proximal cam slot 72a in communication with the channel 70, and a distal cam slot 72b located distally of the proximal cam slot 72a and in communication with the channel 70. The proximal and distal cam slots 72a, 72b are longitudinally spaced from one another and wrap around a central longitudinal axis "X" (FIG. 7) defined by the channel 70 of the tubular shaft 68 of the cam housing 60. The proximal and distal cam slots 72a, 72b each have opposite helical configurations. For example, the proximal cam slot 72a may have a left-handed helical configuration, whereas the distal cam slot 72b may have a right-handed helical configuration, the importance of which being described in detail below. The cam slots 72a, 72b are layed out at a particular pitch such that a set rotation of the tubular shaft 68 results in a defined articulation for the three-bar linkage arrangement.

With reference to FIGS. 7-11, the adapter assembly 20 further includes a pair of first and second axially movable elongate shafts 74, 76 and a pair of first and second articulation links 86, 88. The first and second elongate shafts 74, 76 are disposed on opposite sides of the central longitudinal axis "X" of the cam housing 60. Each of the first and second elongate shafts 74, 76 has a proximal end portion 74a, 76a disposed within the knob housing 22, and a distal end portion 74b, 76b disposed within the outer tube 24.

The proximal end portion 74a of the first elongate shaft 74 has a radially-outwardly extending projection or pin 82 received within the proximal cam slot 72a. The proximal end portion 76a of the second elongate shaft 76 has a radially-outwardly extending projection or pin 84 received in the distal cam slot 72b. Due to the proximal and distal cam slots 72a, 72b of the cam housing 60 having opposing helical configurations (e.g., right-handed vs. left-handed threading), rotation of the cam housing 60 drives the first and second elongate shafts 74, 76 in opposing longitudinal directions.

The first articulation link 86 of the surgical instrument 10 has a proximal end portion 86a pivotably coupled to the distal end portion 74b of the first elongate shaft 74, and the second articulation link 88 has a proximal end portion 88a pivotably coupled to the distal end portion 76b of the second elongate shaft 76. The first and second links 86, 88 each have a distal end portion 86b, 88b pivotably coupled to opposite sides of the collar 32 of the surgical loading unit 30. As such, the opposing longitudinal motion of the first and second elongate shafts 74, 76, induced by a rotation of the cam housing 60, pushes and pulls the corresponding first and second links 86, 88 to articulate the surgical loading unit 30 relative to the adapter assembly 20.

With specific reference to FIGS. 10 and 11, the first articulation link 86 includes an inner-facing surface 90 and the second articulation link 88 includes an inner-facing surface 92 that faces the inner-facing surface 90 of the first link 86. The inner-facing surface 90 of the first link 86 has a concave intermediate portion 90c disposed between a convex proximal end portion 90a of the inner-facing surface 90 and a convex distal end portion 90b of the inner-facing surface 90. Similarly, the inner-facing surface 92 of the second link 88 has a concave intermediate portion 92c disposed between a convex proximal end portion 92a of the inner-facing surface 92 and a convex distal end portion 92b of the inner-facing surface 92. The inner-facing surfaces 90, 92 of the first and second links 86, 88 are configured to guide and support blow-out plates 102a, 102b and a knife shaft 104 of an I-beam assembly 100 of the adapter assembly 20 during articulation of the surgical loading unit 30.

In particular, the concave intermediate portion 90c of the inner-facing surface 90 of the first link 86 is dimensioned to receive a first blow-out plate 102a of the I-beam assembly 100 during articulation of the surgical loading unit 30 in a first direction, indicated by arrow "A" in FIG. 11, whereas the concave intermediate portion 92c of the inner-facing surface 92 of the second link 88 is dimensioned to receive a second blow-out plate 102b of the I-beam assembly 100 during articulation of the surgical loading unit 30 in a second direction, indicated by arrow "B" in FIG. 11.

The convex distal end portions 90b, 92b of the inner-facing surfaces 90, 92 of the first and second links 86, 88 further support the blow-out plates 102a, 102b and the knife shaft 104 of the I-beam assembly 100 during articulation of the surgical loading unit 30. In this way, the inner-facing surfaces 90, 92 of the respective first and second links 86, 88 accommodate the flexing of the knife shaft 104 and blow-out plates 102a, 102b as the surgical loading unit 30 articulates to resist wear and tear of the knife shaft 104 and the blow-out plates 102a, 102b. For example, as best shown in FIG. 11, articulation of the surgical loading unit 30 in the first direction causes the knife shaft 104 and the blow-out plates 102a, 102b to assume a curved shape, whereby the outer blow-out plate (e.g., the first blow-out plate 102a) is guided and supported by the concave intermediate portion 90c of the inner-facing surface 90 of the first link 86, and the inner blow-out plate (e.g., the second blow-out plate 102b) is guided and supported by the convex distal end portion 92b of the inner-facing surface 92 of the second link 88. As can be appreciated, during articulation of the surgical loading unit 30 in the second direction, the first and second links 86, 88 work together in a similar manner to accommodate a flexing of the blow-out plates 102a, 102b and the knife shaft 104.

In operation, to articulate the surgical loading unit 30, the articulation input shaft 50 is rotated via an actuation of the handle assembly 12. The articulation input shaft 50 transfers rotational motion from the gear 56 fixed thereabout to the ring gear 58 via the spur gear cluster 64. Since the cam housing 60 is fixed to the ring gear 58, the cam housing 60 rotates with the ring gear 58 about the central longitudinal axis "X." As the cam housing 60 rotates, the proximal cam slot 72a of the cam housing 60 drives the pin 82 of the first elongate shaft 74 through the proximal cam slot 72 in a distal direction, indicated by arrow "C" in FIG. 7, and the distal cam slot 72b of the cam housing 60 drives the pin 84 of the second elongate shaft 76 through the distal cam slot 72b in a proximal direction, indicated by arrow "D" in FIG. 7.

Due to the first articulation link 86 acting as a pivotable coupling between the first elongate shaft 74 of the adapter assembly 20 and the first side of the surgical loading unit 30, and the second link 88 acting as a pivotable coupling between the second elongate shaft 76 of the adapter assembly 20 and the second side of the surgical loading unit 30, distal movement of the first elongate shaft 74 and proximal movement of the second elongate shaft 76 drives an articulation of the surgical loading unit 30 in the first direction indicated by arrow "A" in FIG. 11. Similarly, proximal movement of the first elongate shaft 74 and distal movement of the second elongate shaft 76 drives an articulation of the surgical loading unit 30 in the second direction indicated by arrow "B" in FIG. 11.

With reference to FIGS. 12-16, the firing and clamping mechanism of the adapter assembly 20 will now be described. The firing input shaft 52 of the adapter assembly 20 is centrally located between the articulation and rotation input shafts 50, 54 and is configured to effect a clamping and stapling function of the surgical loading unit 30. The firing input shaft 52 has a proximal end portion 52a configured to be drivingly coupled to the drive member 13b of the handle assembly 12 to drive a rotation of the firing input shaft 52. It is contemplated that the firing input shaft 52 may be configured as a drive screw having a threaded outer surface 106.

The adapter assembly 20 further includes an I-beam assembly 100, briefly described above, having a nut 108, a firing rod or tube 110, and a knife shaft 104. The nut 108 of the I-beam assembly 100 is disposed within the tubular shaft 68 of the cam housing 60 and is keyed to an inner tube 112, such that rotation of the nut 108 within the inner tube 112 is prevented during rotation of the firing input shaft 52. The nut 108 being disposed within the cam housing 60 of the articulation mechanism gives the adapter assembly 20 a compact design.

The firing rod 110 of the I-beam assembly 100 has a proximal end portion 110a fixed to the nut 108, and a distal end portion 110b fixed to a proximal end portion 104a of the knife shaft 104 of the I-beam assembly 100. In embodiments, the nut 108 may be directly attached to the proximal end portion 104a of the knife shaft 104 rather than be coupled via the firing rod 110. Since the knife shaft 104 of the I-beam assembly 100 is fixed to the nut 108, axial movement of the nut 108 through the outer tube 24, in response to a rotation of the firing input shaft 52, drives an axial movement of the knife shaft 104.

With reference to FIGS. 15, 16A, and 16B, the knife shaft 104 of the I-beam assembly includes a plurality of stacked elongated, rectangular blades 114. The plurality of blades 114 have an upper portion 114a extending through a longitudinally-extending slot 116 defined in the anvil plate 36, and a lower portion 114b extending through a longitudinally-extending slot 118 defined in the chassis 38 of the staple cartridge assembly 37. As shown in FIG. 15, the upper portion 114a of the blades 114 overlap with the anvil plate 36, and the lower portion 114b of the blades 114 overlap with the chassis 38. It is contemplated that this overlapping arrangement prevents buckling of the knife shaft 104 during firing.

The knife shaft 104 of the I-beam assembly 100 has a distal end portion 104b disposed within the surgical loading unit 30. The distal end portion 104b of the knife shaft 104 is configured to pivot the staple cartridge assembly 37 toward the anvil plate 36 during distal advancement of the knife shaft 104. The distal end portion 104b of the knife shaft 104 has an upper foot 120 disposed within a channel 121 defined by the anvil plate 36, a lower foot 122 disposed outside of the chassis 38 of the staple cartridge assembly 37, and a sharp distally-oriented surface 124 extending between the upper and lower foots 120, 122. The distally-oriented surface 124 is configured to sever tissue during distal advancement thereof through the end effector 34.

In operation, to fire and clamp the surgical loading unit 30, the firing input shaft 52 is rotated via an actuation of the handle assembly 12 attached to the coupling mechanism 25 of the adapter assembly 20. The firing input shaft 52 drives a translation of the nut 108 in a distal direction, indicated by arrow "C" in FIG. 13, relative to the firing input shaft 52. Given that the I-beam assembly 100, including the nut 108, the firing rod 110, and the knife shaft 104, is one integral unit, the firing rod 110 and the knife shaft 104 advance distally with the nut 108. The distal end portion 104b of the knife shaft 104 of the I-beam assembly 100 advances distally through the anvil plate 36 and the chassis 38 to pivot the chassis 38 toward the anvil plate 36. As the distal end portion 104b of the knife shaft 104 advances distally through the anvil plate 36 and the chassis 38, any tissue disposed therebetween is severed by the sharp, distally-oriented surface 124 of the knife shaft 104.

Figure 17:
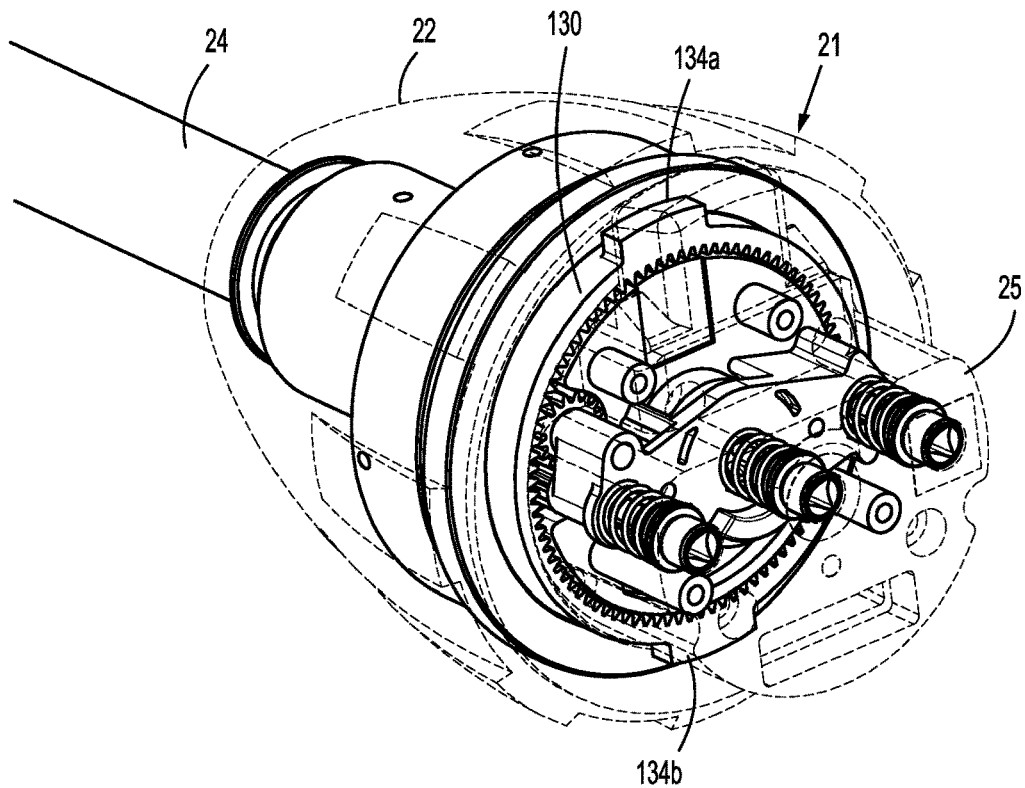
FIG. 17 is a rear, perspective view of the adapter assembly of FIG. 1A, with the outer housing shown in phantom.
Figure 18:
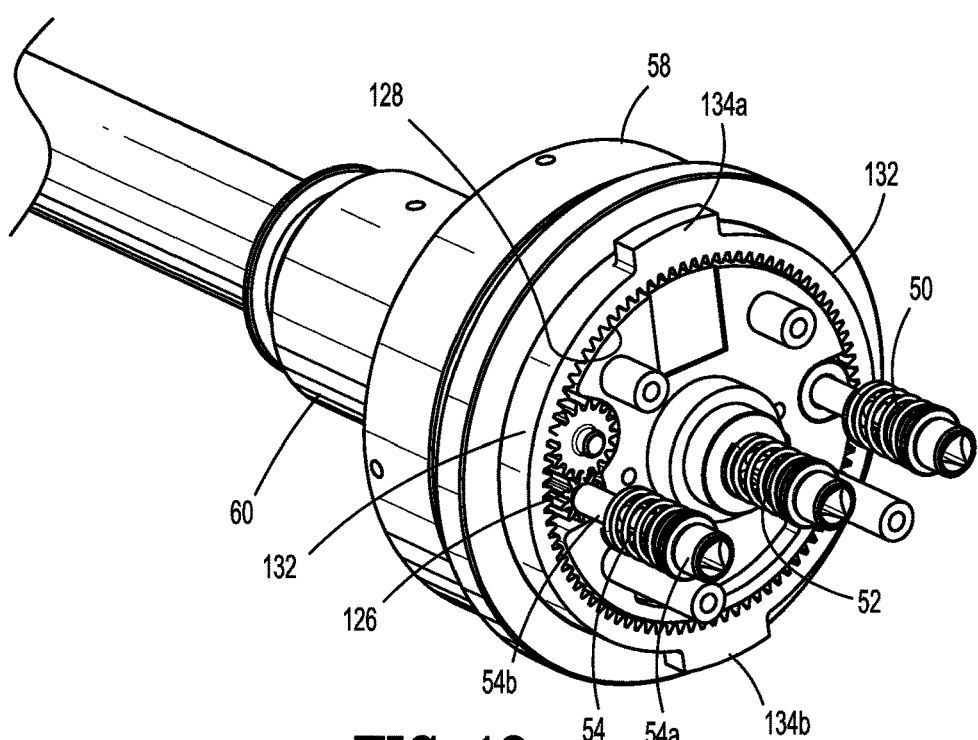
FIG. 18 is a rear, perspective view of internal components of the adapter assembly of FIG. 17.

With reference to FIGS. 17 and 18, the rotation mechanism of the adapter assembly 20 will now be described. The rotation input shaft 54 of the adapter assembly 20 has a proximal end portion 54a configured to be drivingly coupled to a drive member 13c of the handle assembly 12 to drive a rotation of the rotation input shaft 54. The rotation input shaft 54 has a gear 126 fixed about a distal end portion 54b thereof. The gear 126 of the rotation input shaft 54 is operably coupled to teeth 128 of a rotation ring gear 130 via an idler gear 132. In embodiments, the gear 126 of the rotation input shaft 54 may directly interface with the rotation ring gear 130.

The rotation ring gear 130 has a pair of tabs 134a, 134b extending radially outward from opposite radial positions of the rotation ring gear 130. The tabs 134a, 134b of the rotation ring gear 130 interlock with corresponding recesses (not explicitly shown) defined in an inner surface of the knob housing 22, such that the knob housing 22 is rotatable with the rotation ring gear 130 relative to the coupling mechanism 25. In embodiments, the rotation ring gear 130 may have any suitable feature that fastens the rotation ring gear 130 to the knob housing 22, such as, for example, threaded engagement, frictional engagement, lock and key engagement, latches, buttons, bayonet-type connections, welding, adhesives and/or other mechanisms.

In operation, to rotate the surgical loading unit 30, the rotation input shaft 54 is rotated via an actuation of the handle assembly 12 attached to the coupling mechanism 25 of the adapter assembly 20. Rotational motion of the rotation input shaft 54 is transferred to the rotation ring gear 130 via the idler gear 132. Since the tabs 134a, 134b of the rotation ring gear 130 lock the knob housing 22 thereto, rotation of the rotation ring gear 130 results in a rotation of the knob housing 22 relative to the coupling mechanism 25 and around the input shafts 50, 52, 54. The outer tube 24 of the adapter assembly 20 is fastened to the knob housing 22 and, as such, rotates with the knob housing 22, which, in turn, causes the surgical loading unit 30 to rotate about the longitudinal axis of the adapter assembly 20.

Turning now to FIGS. 19-28, another embodiment of an adapter assembly is shown and is generally referred to by reference character 200. Adapter assembly 200 has several identical or similar components as those discussed hereinabove with regard to adapter assembly 20. Accordingly, many of the features of adapter assembly 200 will not be discussed in further detail. Additionally, features that are common to both adapter assembly 20 and adapter assembly 200 may be referred to by the same reference number.

Figure 19:
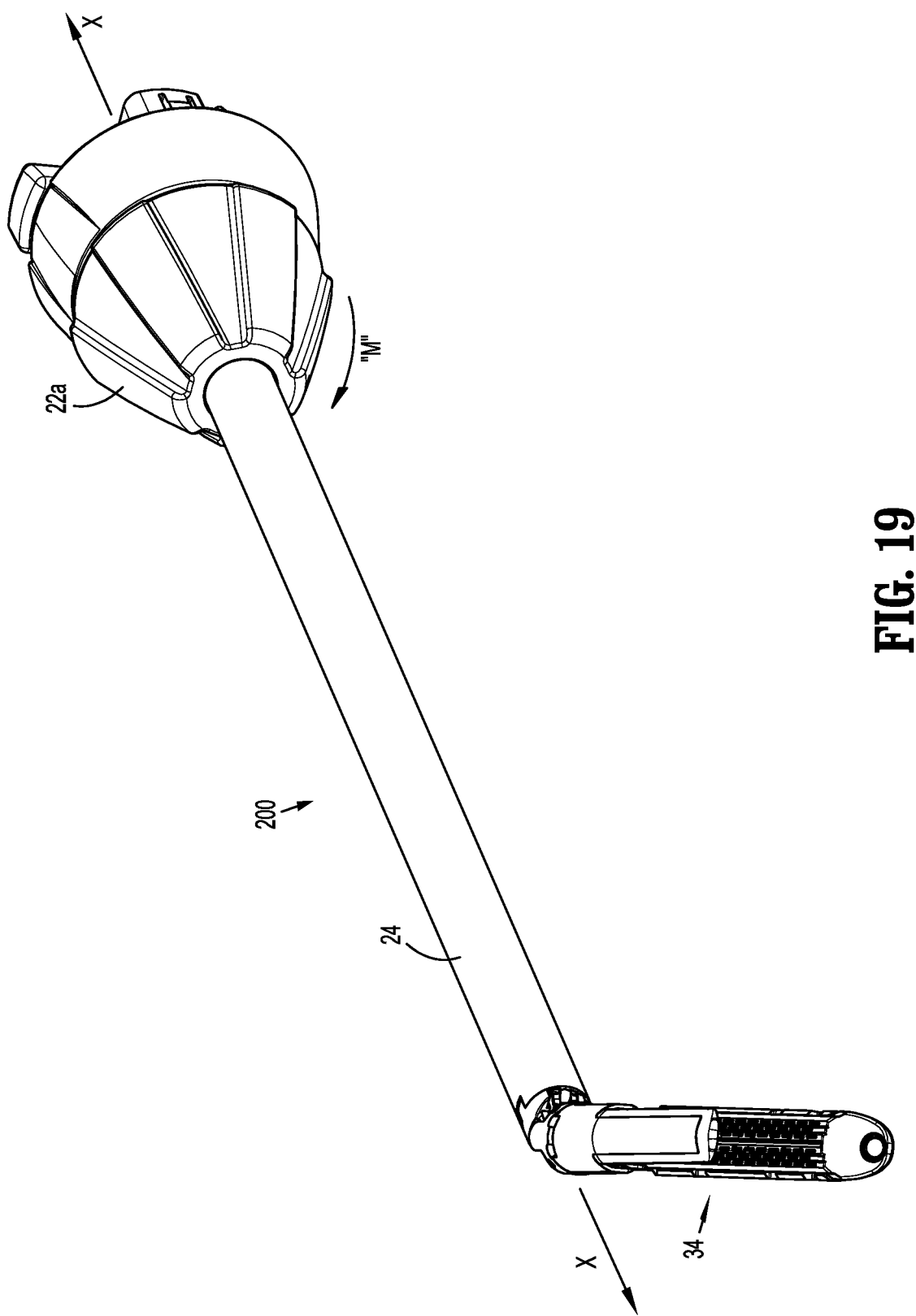
FIG. 19 is a perspective view of an adapter assembly in accordance with another embodiment of the present disclosure.
Figure 21:
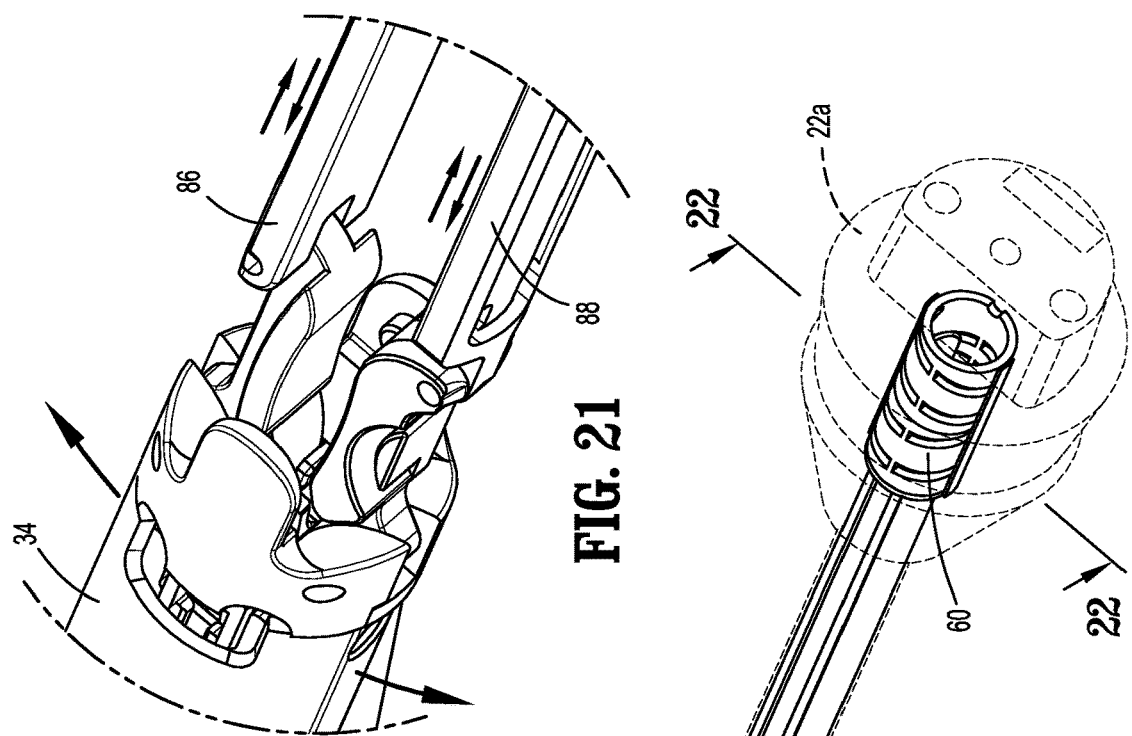
FIG. 21 is an enlarged view of the area detailed in FIG. 20.

Adapter assembly 200 includes structure to help limit, prevent or correct unintentional articulation of the end effector 34. For instance, during manual rotation of knob housing 22a to rotate end effector 34 and outer tube 24 about the central longitudinal axis "X," for instance, the angle of articulation of end effector 34 may also change. As shown in FIG. 19, this unintentional change in the angle of articulation of end effector 34 may occur during manual rotation of the knob housing 22a in the general direction of arrow "M," when the cam housing 60 remains in its rotational position (e.g., due to the engagement between the articulation input shaft 50 and an associated drive member 13a of the handle assembly 12) (see FIGS. 1A, 1B and 22). Knob housing 22a is non-rotationally connected to a distal bushing 22b which is non-rotationally connected to ring gear 58. In this manner, manual rotation of knob housing 22a results in rotation of distal bushing 22b, and in turn rotation of ring gear 58.

Figure 20:
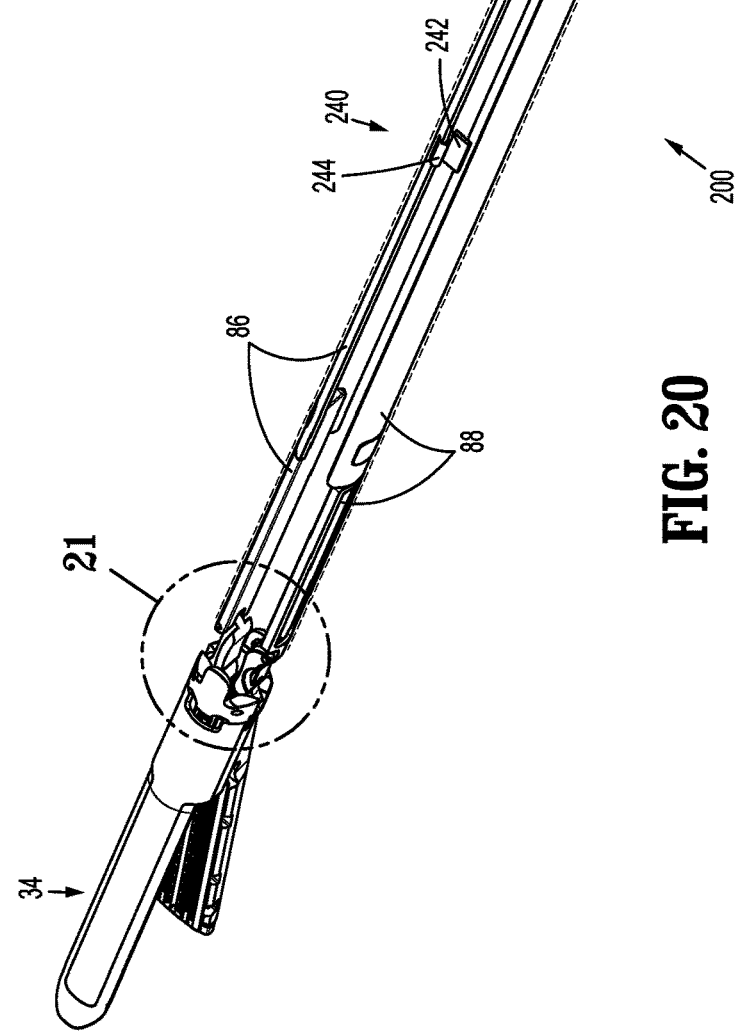
FIG. 20 is a perspective view of the adapter assembly of FIG. 19 with portions thereof omitted.
Figure 23:
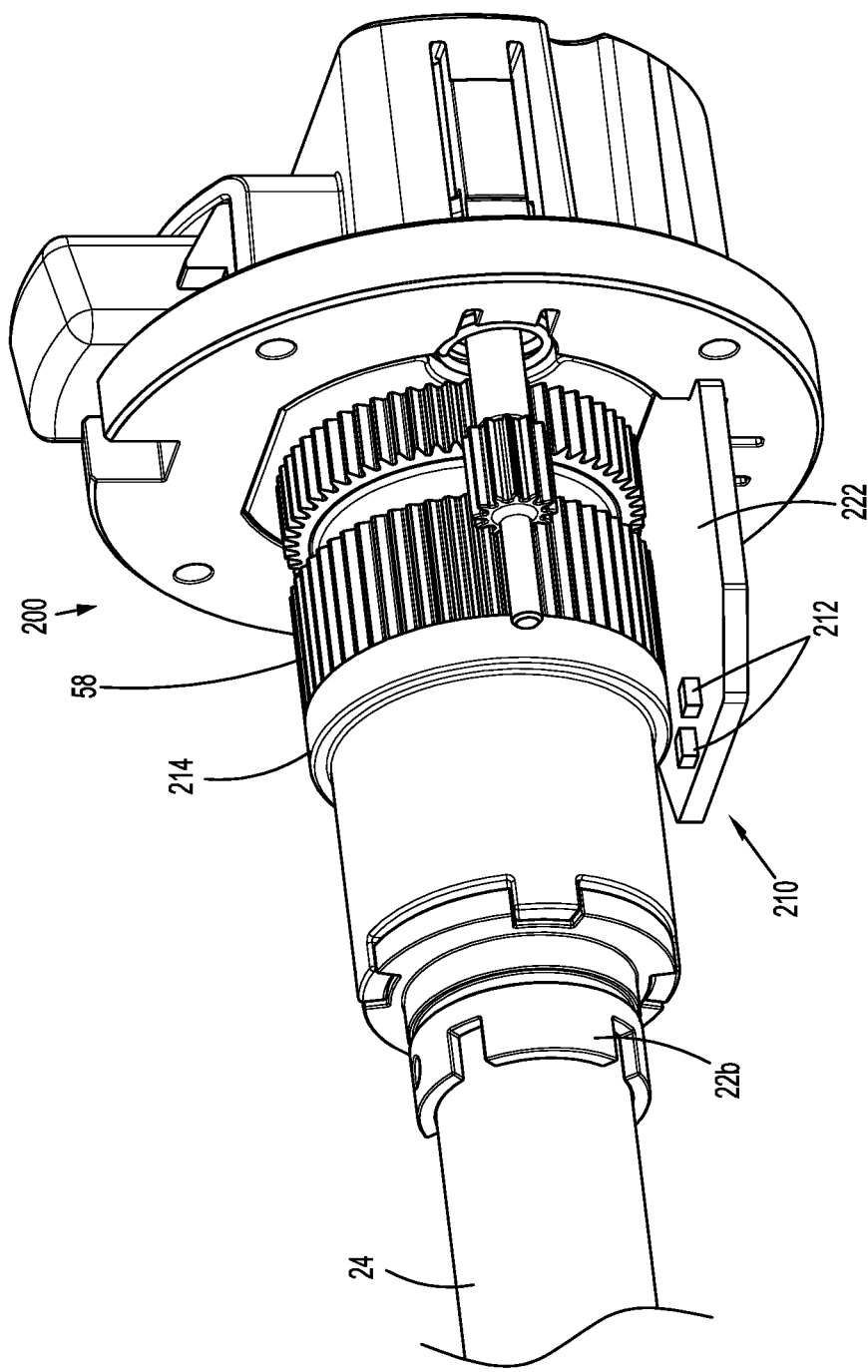
FIG. 23 is a perspective view of internal components within a proximal section of the adapter assembly of FIGS. 19-22.
Figure 24:
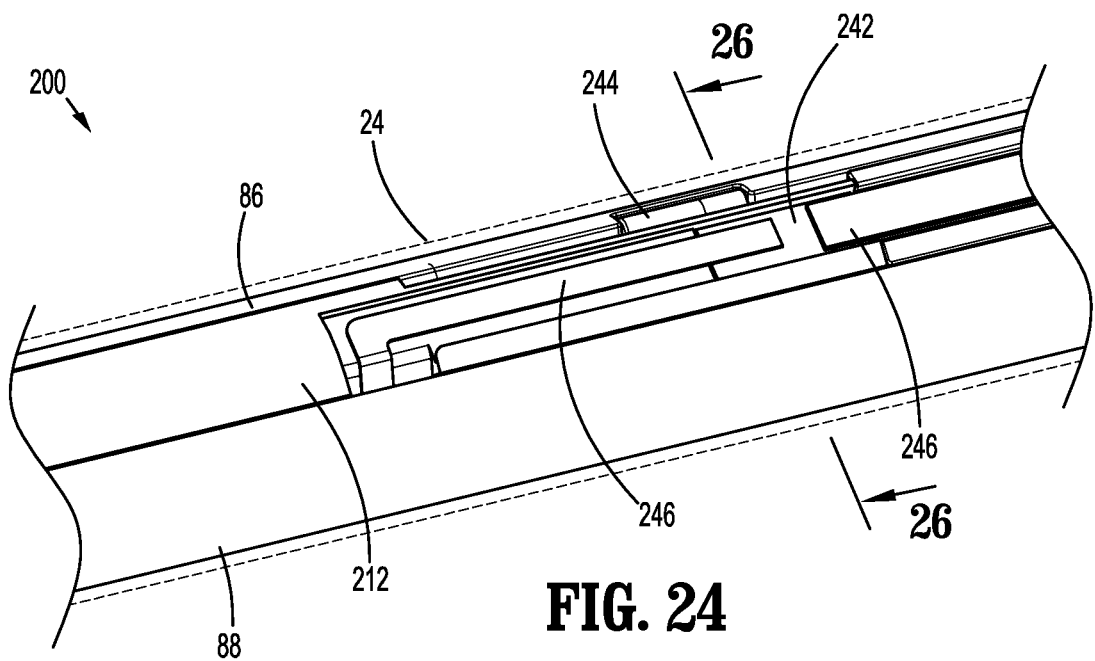
FIG. 24 is a perspective view of a sensor assembly of the adapter assembly of FIGS. 19-23.
Figure 25:
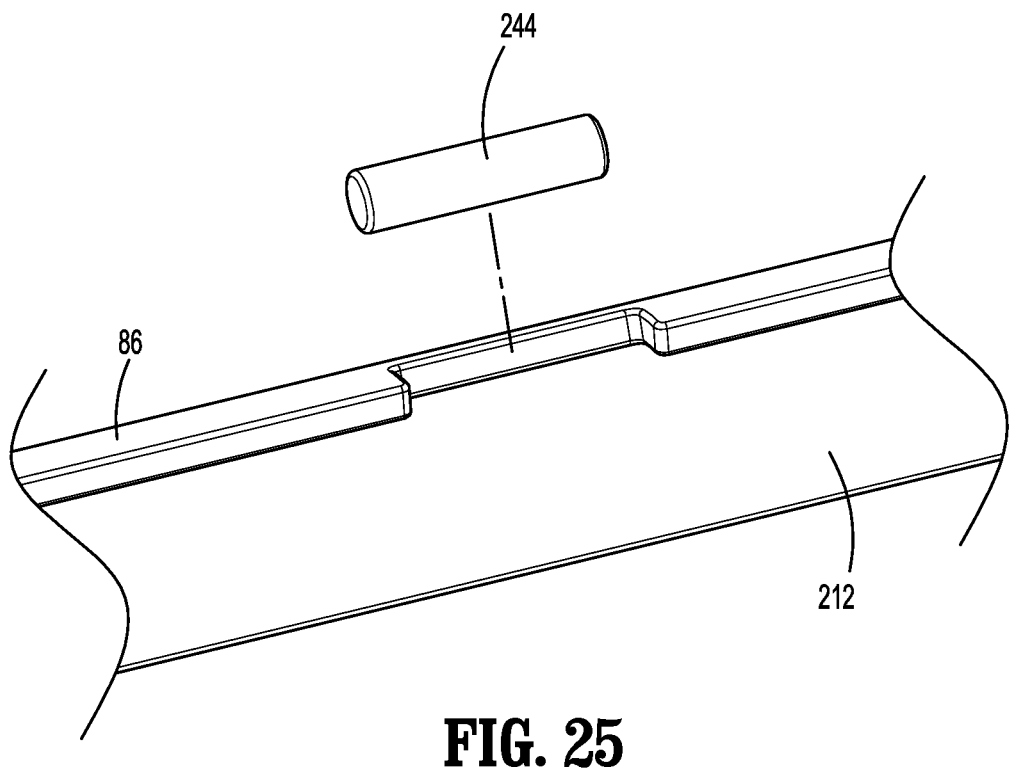
FIG. 25 is a perspective, assembly view of a portion of the sensor assembly of FIG. 24.
Figure 26:
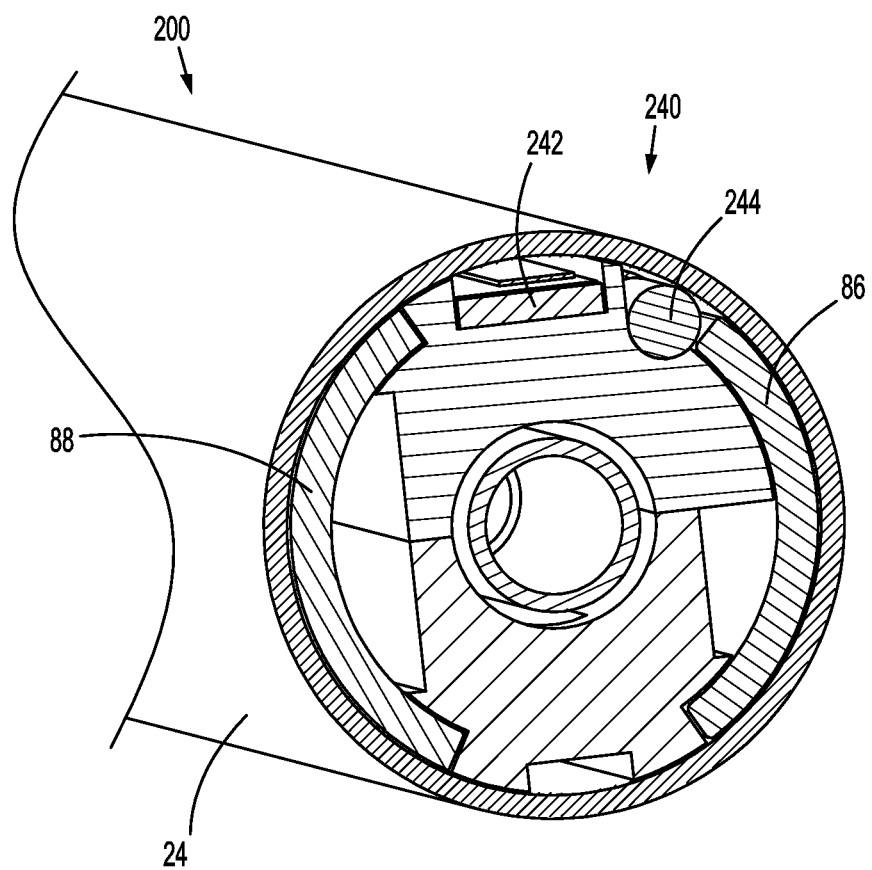
FIG. 26 is a cut-away view of the sensor assembly and adapter assembly along line 24-24 in FIG. 24.

Referring now to FIG. 23, a sensor assembly 210 may be used to determine whether the articulation movement is unintentional, such as during manual rotation of the knob housing 22a (FIGS. 19 and 20). Here, the sensor assembly 210 includes sensors 212 (e.g., Hall effect sensors) and a magnet 214 (e.g., a refrigerator-type magnet or magnet having appropriately alternating north/south oriented poles). The sensors 212 are mounted in quadrature on a printed circuit board 222 within adapter assembly 200. The magnet 214 is mounted to, and circumferentially around, the ring gear 58 at a location that is detectable by sensors 212, as shown in FIG. 23. The sensors 212 relay the information relating to the rotation of the ring gear 58 to a controller or software 220 on the printed circuit board 222, to signify a manual rotation of the knob housing 22, and thus an unintentional articulation of the end effector 34.

To help limit, prevent or correct the unintentional articulation of the end effector 34, the adapter assembly 200 includes software 220, and at least one sensor assembly, as discussed below. Generally, the sensor assembly detects unintentional movement of first and/or second articulation links 86, 88, communicates with the software 220, and the software 220 sends a signal to the drive member 13a (or a different motor) to make the necessary adjustments to return the first and/or second articulation links 86, 88 (and accompanying sensor assembly or portion thereof) to the desired position (see FIG. 21).

Figure 22:
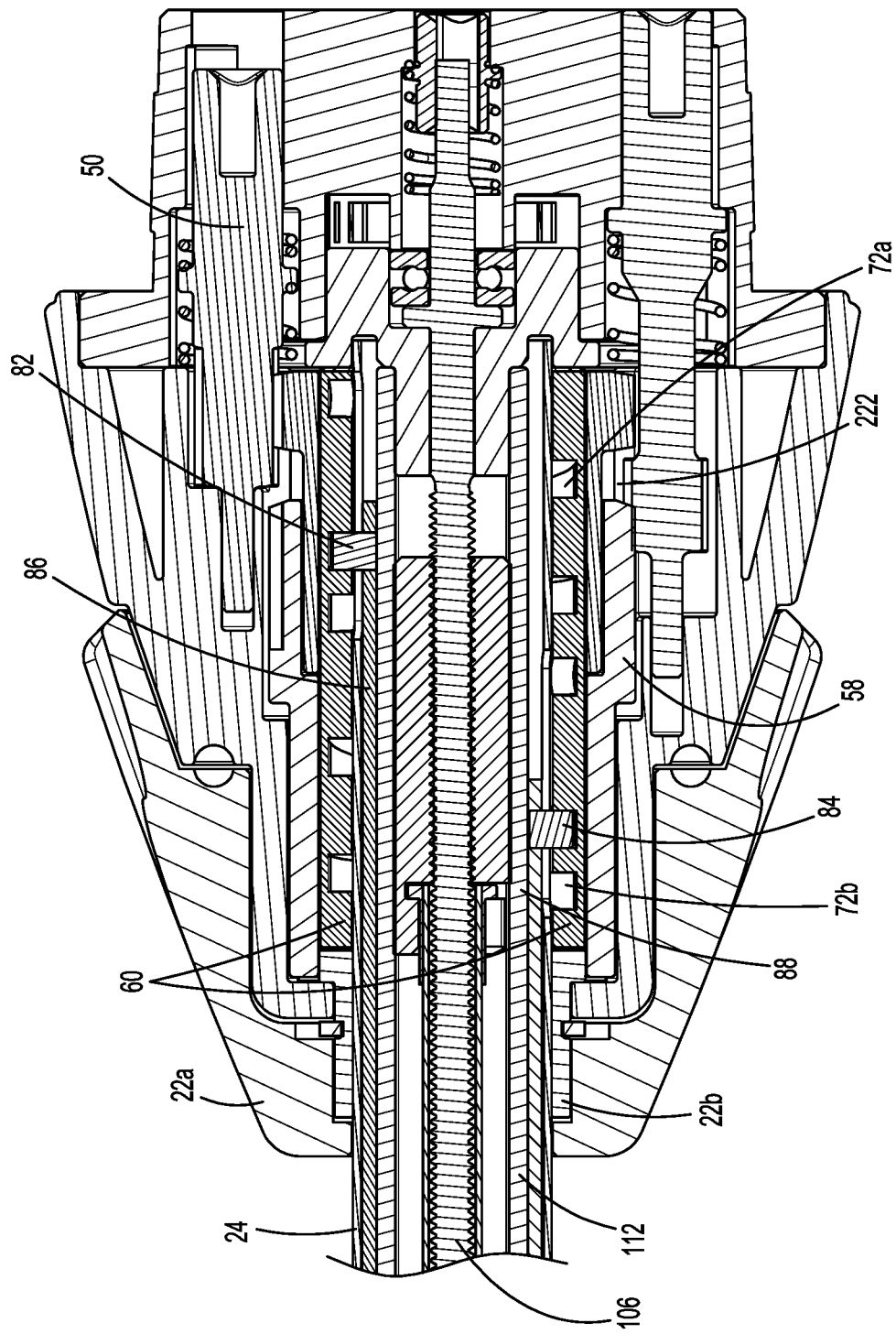
FIG. 22 is a side, cross-sectional view of a proximal section of the adapter assembly taken along section line 22-22 in FIG. 20.

The software 220 may be included on a printed circuit board 222 that is located on or within a portion of surgical instrument 10, and may communicate with the sensor assembly(ies) and/or drive member 13a (FIG. 1B) with electrical connections such as pins, ribbons, or wires, or may communicate wirelessly. For example, FIGS. 22 and 23 illustrate the printed circuit board 222 within adapter assembly 200. Alternatively, the software 220 may be located at a remote location and communicate with the sensor assembly (ies) and/or drive member 13a wirelessly.

A variety of different types of sensor assemblies may be used in connection with adapter assembly 200 to detect movement of the first and/or second articulation links 86, 88. For instance, adapter assembly 200 may include a giant magnetoresistive (GMR) sensor, a flat resistive sensor, a potentiometer sensor, an optical sensor, a sonar sensor, an inductive sensor, and/or other suitable sensors.

With particular reference to FIGS. 20 and 24-26 adapter assembly 200 is shown including a first type of sensor assembly 240, which includes a magnetic or GMR sensor 242 and a corresponding magnet 244. The GMR sensor 242 (e.g., model number AAK001-14E, manufactured by NVE Corporation) is disposed at least partially within an inner tube 212 of the adapter assembly 200. The magnet 244 is disposed in engagement with the first articulation link 86. GMR sensor 242 is electrically connected to software 220 (e.g., in the printed circuit board 222 or controller) via electrical ribbon 246 (FIG. 22). Since the first and second articulation links 86, 88 move together (in opposite directions), the inclusion of the magnet 244 in engagement with a single articulation link is effective. The present disclosure also includes embodiments where the GMR sensor 242 is disposed in engagement with the first articulation link 86, and the magnet is disposed at least partially within the inner tube 212 of the adapter assembly 200.

In use, GMR sensor 242 senses the position of the magnet 244 (and thus first articulation link 86) relative thereto. The relative position (or displacement) of the magnet 244 and the first articulation link 86 corresponds to the amount of articulation of the end effector 34, as discussed above. This positional information is relayed to the software 220. The software 220 includes data regarding the desired amount of articulation of the end effector 34, and the associated desired position of the first articulation link 86/magnet 244. The desired amount of articulation of the end effector 34 can be ascertained by analyzing the amount of rotation of the articulation input shaft 50.

Next, the software 220 compares the actual, measured position of the magnet 244 with the desired portion of the magnet 244, and sends a signal to drive member 13a to move the first articulation link 86 a sufficient distance proximally or distally such that the desired position of the first articulation link 86, and thus the desired amount of articulation of the end effector 34 is achieved. Additionally, the software 220 is capable of constantly or servo controlling the drive member 13a to help ensure non-desired articulation of the end effector 34 is limited.

Referring now to FIGS. 27 and 28, adapter assembly 200 is shown including a second type of sensor assembly 250, which includes a thin-pot resistive senor 252 and a corresponding biasing element (e.g., leaf spring 260). Sensor assembly 250 is used to determine the longitudinal position of the first articulation link 86 relative to the inner tube 212 of the adapter assembly 200. The sensor 252 is disposed at least partially within the inner tube 212 of the adapter assembly 200, and the leaf spring 260 is disposed in engagement with the first articulation link 86, such that the leaf spring 260 is in contact with the sensor 252 and is configured to slidingly engage the sensor 252. The sensor 252 is in communication with the software 220 (e.g., in the printed circuit board 222 or controller) via wireless communication, for instance. Since the first and second articulation links 86, 88 move together (in opposite directions), the inclusion of the leaf spring 260 in engagement with a single articulation link is effective. The present disclosure also includes embodiments where the sensor 252 disposed in engaged with the first articulation link 86, and the leaf spring 260 is disposed at least partially within the inner tube 212 of the adapter assembly 200.

In use, the sensor 252 senses the position of the leaf spring 260 (and thus first articulation link 86) relative thereto. The relative position (or displacement) of the leaf spring 260 and the first articulation link 86 corresponds directly to the amount of articulation of the end effector 34, as discussed above. This positional information is relayed to the software 220. The software 220 includes data regarding the desired amount of articulation of the end effector 34, and the associated desired position of the first articulation link 86/leaf spring 260. The desired amount of articulation of the end effector 34 can be ascertained or calculated by analyzing the amount of rotation of the articulation input shaft 50 and/or the amount of linear displacement of the first articulation link 86 and or the second articulation link 88.

Next, the software 220 compares the actual, measured position of the leaf spring 260 with the desired portion of the leaf spring 260, and sends a signal to the drive member 13a to move the first articulation link 86 a sufficient distance proximally or distally such that the desired position of the first articulation link 86, and thus the desired amount of articulation of the end effector 34 is achieved. Additionally, the software 220 is capable of constantly or servo controlling the drive member 13a to help ensure non-desired articulation of the end effector 34 is limited.

It is also envisioned that drive member 13a includes an encoder that can be monitored during use. Here, if the drive member 13a is mechanically backdriven during rotation of knob 22, the driver member 13a can automatically correct its position such that the amount of non-desired articulation of the end effector 34 is limited.

Persons skilled in the art will understand that the adapter assemblies and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An adapter assembly configured to mechanically engage a surgical instrument, comprising:
  a knob housing;
  an outer tube extending distally from the knob housing and defining a longitudinal axis;
  an end effector extending distally from the outer tube, the end effector is movable from a first position where the end effector is aligned with the longitudinal axis, to a second position where the end effector is disposed at an angle relative to the longitudinal axis;
  an articulation link extending through at least a portion of the outer tube and disposed in mechanical cooperation with the end effector;
  a ring gear disposed at least partially within the knob housing, wherein rotation of the ring gear about the longitudinal axis causes longitudinal translation of the articulation link relative to the outer tube, which causes the end effector to move from its first position to its second position; and a sensor assembly including a first portion disposed in mechanical cooperation with the articulation link, and a second portion disposed at least partially within the outer tube, the sensor assembly configured to determine an actual amount of articulation of the end effector based on a distance the articulation link moves longitudinally relative to the outer tube.

2. The adapter assembly according to claim 1, wherein the sensor assembly is configured to communicate with software, and wherein the software compares the actual amount of articulation of the end effector with a desired amount of articulation of the end effector.

3. The adapter assembly according to claim 2, wherein the software is disposed on a printed circuit board disposed at least partially within the knob housing.

4. The adapter assembly according to claim 1, wherein one of the first portion or the second portion of the sensor assembly is a magnet, and wherein the other of the first portion or the second portion of the sensor assembly is a magnetoresistive sensor.

5. The adapter assembly according to claim 1, wherein one of the first portion or the second portion of the sensor assembly is a leaf spring, and wherein the other of the first portion or the second portion of the sensor assembly is a thin-pot resistive senor.

6. The adapter assembly according to claim 1, further comprising a second sensor assembly disposed at least partially within the knob housing, the second sensor assembly configured to detect manual rotation of the knob housing relative to the outer tube.

7. The adapter assembly according to claim 6, wherein the second sensor assembly includes at least one sensor and at least one magnet.

8. The adapter assembly according to claim 7, wherein the at least one sensor of the second sensor assembly includes at least two Hall effect sensors.

9. The adapter assembly according to claim 8, wherein the at least one magnet of the second sensor assembly includes a refrigerator-type magnet.

10. The adapter assembly according to claim 9, wherein the software is disposed on a printed circuit board disposed at least partially within the knob housing, and wherein the at least two Hall effect sensors are disposed on the printed circuit board.

11. A surgical instrument, comprising:
a handle assembly including a first drive member; and
an adapter assembly configured to selectively engage the handle assembly, the adapter assembly including:
a knob housing;
an outer tube extending distally from the knob housing and defining a longitudinal axis;
an end effector extending distally from the outer tube, the end effector is movable from a first position where the end effector is aligned with the longitudinal axis, to a second position where the end effector is disposed at an angle relative to the longitudinal axis;
an articulation link extending through at least a portion of the outer tube and disposed in mechanical cooperation with the end effector, wherein longitudinal translation of the articulation link relative to the outer tube causes the end effector to move from its first position to its second position;
a ring gear disposed at least partially within the knob housing and in mechanical cooperation with the first drive member when the adapter assembly is engaged with the handle assembly, wherein rotation of the first drive member causes rotation of the ring gear about the longitudinal axis, which causes longitudinal translation of the articulation link; and
a sensor assembly including a first portion disposed in mechanical cooperation with the articulation link, and a second portion disposed at least partially within the outer tube, the sensor assembly configured to determine an actual amount of articulation of the end effector based on a distance the articulation link moves longitudinally relative to the outer tube.

12. The surgical instrument according to claim 11, wherein manual rotation of the knob housing relative to the outer tube causes undesired articulation of the end effector.

13. The surgical instrument according to claim 12, wherein the sensor assembly is configured to communicate with software, and wherein the software compares the actual amount of articulation of the end effector with a desired amount of articulation of the end effector.

14. The surgical instrument according to claim 13, wherein the software is configured to instruct the first drive member of the surgical instrument to move the articulation link such that the actual articulation of the end effector equals the desired articulation of the end effector.

15. The surgical instrument according to claim 12, further comprising a second sensor assembly disposed at least partially within the knob housing, the second sensor assembly configured to detect manual rotation of the knob housing relative to the outer tube.

16. The surgical instrument according to claim 15, wherein the second sensor assembly includes at least one sensor and at least one magnet.

17. The surgical instrument according to claim 16, wherein the at least one sensor of the second sensor assembly includes at least two Hall effect sensors.

18. The surgical instrument according to claim 17, wherein the at least one magnet of the second sensor assembly includes a refrigerator-type magnet.

19. The surgical instrument according to claim 11, wherein one of the first portion or the second portion of the sensor assembly is a magnet, and wherein the other of the first portion or the second portion of the sensor assembly is a magnetoresistive sensor.

20. The surgical instrument according to claim 11, wherein one of the first portion or the second portion of the sensor assembly is a leaf spring, and wherein the other of the first portion or the second portion of the sensor assembly is a thin-pot resistive senor.

* * * * *